(12) United States Patent
Gregory et al.

(10) Patent No.: US 9,511,093 B2
(45) Date of Patent: *Dec. 6, 2016

(54) COMPOSITIONS OF MESENCHYMAL STEM CELLS TO REGENERATE BONE

(75) Inventors: Carl A. Gregory, Temple, TX (US); Darwin J. Prockop, Philadelphia, PA (US)

(73) Assignee: The Texas A & M University System, College Station, TX (US)

( * ) Notice: Subject to any disclaimer, the term of this patent is extended or adjusted under 35 U.S.C. 154(b) by 435 days.

This patent is subject to a terminal disclaimer.

(21) Appl. No.: 12/730,022

(22) Filed: Mar. 23, 2010

(65) Prior Publication Data
US 2010/0247494 A1 Sep. 30, 2010

Related U.S. Application Data

(60) Provisional application No. 61/210,764, filed on Mar. 23, 2009.

(51) Int. Cl.
| *A01N 63/00* | (2006.01) |
| *A01N 65/00* | (2009.01) |
| *C12N 5/00* | (2006.01) |
| *C12N 5/02* | (2006.01) |
| *A61K 35/28* | (2015.01) |
| *C12N 5/0775* | (2010.01) |
| *A61K 35/12* | (2015.01) |

(52) U.S. Cl.
CPC ............. *A61K 35/28* (2013.01); *C12N 5/0663* (2013.01); *A61K 2035/124* (2013.01); *C12N 2501/385* (2013.01); *C12N 2501/415* (2013.01)

(58) Field of Classification Search
None
See application file for complete search history.

(56) References Cited

U.S. PATENT DOCUMENTS

| 4,352,883 A | 10/1982 | Lim |
| 4,353,888 A | 10/1982 | Sefton |
| 4,678,470 A | 7/1987 | Nashef et al. |
| 4,968,733 A | 11/1990 | Muller et al. |
| 4,976,859 A | 12/1990 | Wechs |
| 5,041,138 A | 8/1991 | Vacanti et al. |
| 5,082,670 A | 1/1992 | Gage et al. |
| 5,084,350 A | 1/1992 | Chang et al. |
| 5,144,016 A | 9/1992 | Skjak-Braek et al. |
| 5,158,881 A | 10/1992 | Aebischer et al. |
| 5,284,761 A | 2/1994 | Aebischer et al. |
| 5,516,532 A | 5/1996 | Atala et al. |
| 5,536,656 A | 7/1996 | Kemp et al. |
| 5,571,083 A | 11/1996 | Lemelson |
| 5,618,531 A | 4/1997 | Cherksey |
| 5,709,854 A | 1/1998 | Griffith-Cima et al. |
| 5,723,331 A | 3/1998 | Tubo et al. |
| 5,736,372 A | 4/1998 | Vacanti et al. |
| 5,741,685 A | 4/1998 | Vacanti |
| 5,759,830 A | 6/1998 | Vacanti et al. |
| 5,770,193 A | 6/1998 | Vacanti et al. |
| 5,770,417 A | 6/1998 | Vacanti et al. |
| 5,804,178 A | 9/1998 | Vacanti et al. |
| 5,855,610 A | 1/1999 | Vacanti et al. |
| 5,863,531 A | 1/1999 | Naughton et al. |
| 5,902,741 A | 5/1999 | Purchio et al. |
| 5,944,754 A | 8/1999 | Vacanti |
| 6,027,744 A | 2/2000 | Vacanti et al. |
| 6,123,727 A | 9/2000 | Vacanti et al. |
| 6,139,574 A | 10/2000 | Vacanti et al. |
| 6,143,501 A | 11/2000 | Sittinger et al. |
| 6,498,018 B1 | 12/2002 | Carpenter |
| 7,175,839 B1* | 2/2007 | Hiserodt ................. 424/93.1 |
| 2002/0054901 A1* | 5/2002 | Gainey et al. ............. 424/426 |
| 2004/0175366 A1 | 9/2004 | Badylak |
| 2004/0176855 A1 | 9/2004 | Badylak |
| 2005/0013870 A1 | 1/2005 | Freyman et al. |
| 2005/0013872 A1 | 1/2005 | Freyman |
| 2005/0025838 A1 | 2/2005 | Badylak |
| 2005/0043819 A1 | 2/2005 | Schmidt et al. |
| 2005/0054663 A1* | 3/2005 | Bennett et al. ............. 514/269 |
| 2005/0084494 A1* | 4/2005 | Prockop et al. ........... 424/146.1 |
| 2005/0181016 A1 | 8/2005 | Freyman et al. |
| 2005/0203636 A1 | 9/2005 | McFetridge |
| 2005/0256588 A1 | 11/2005 | Sawa et al. |
| 2005/0261181 A1* | 11/2005 | Wu et al. .................. 514/12 |
| 2006/0147433 A1 | 7/2006 | Hiles |
| 2009/0054983 A1* | 2/2009 | Wuisman et al. ......... 623/16.11 |

FOREIGN PATENT DOCUMENTS

| WO | WO-92/19195 A1 | 11/1992 |
| WO | WO-95/05452 A2 | 2/1995 |

OTHER PUBLICATIONS

Castano-Izquierdo et al., J. Biomedic. Mater. Res., 82A(1):129-138 (2007).*
Temenoff et al., Wiley InterScience, pp. 235-244 (2004).*
Gregory et al., Exp. Cell Res., 306:330-335 (2005).*
Gregory et al., J. Biol. Chem., 280:2309-2323 (2005).*
de Boer et al., Bone, 34:818-826 (2004).*
Wei et al., Arth. Rheum., 63(6):1707-1717 (2011).*
Akune et al., "PPARgamma insufficiency enhances osteogenesis through osteoblast formation from bone marrow progenitors." 2004, J Clin Invest 113:846-855.

(Continued)

Primary Examiner — Thomas J Visone
(74) Attorney, Agent, or Firm — Gardere Wynne Sewell LLP

(57) ABSTRACT

The present invention encompasses an osteogenic composition comprising mesenchymal stem cells pre-cultured in the presence of an agent that accelerates canonical Wnt signaling therein. Also, provided are osteogenic compositions incorporated into a biocompatible gel. The present invention provides methods for treating bone degeneration or injury associated with a pathophysiological condition in a mammal or for accelerating repair of a skeletal injury in a mammal by administering to the mammal or contacting the site of injury with the osteogenic composition.

19 Claims, 28 Drawing Sheets

(56) References Cited

OTHER PUBLICATIONS

Bain et al., "Activated beta-catenin induces osteoblast differentiation of C3H10T1/2 cells and participates in BMP2 mediated signal transduction." 2003, Biochem Biophys Res Commun 301:84-91.

Boland et al., "Wnt 3a promotes proliferation and suppresses osteogenic differentiation of adult human mesenchymal stem cells." 2004, J Cell Biochem 93:1210-30.

Boyden et al., "High bone density due to a mutation in LDL-receptor-related protein 5." 2002, N Eng J Med 346:1513-1521.

Castano-Izquierdo, et al., "Pre-culture period of mesenchymal stem cells in osteogenic media influences their in vivo bone forming potential." 2007, Journal of Biomedical Materials Research Part A 82(1):129-138.

Damiens et al., "Anti-mitotic properties of indirubin-3'-monoxime, a CDK/GSK-3 inhibitor: induction of endoreplication following prophase arrest." 2001, Oncogene 20:3786-3797.

Farmer, "Regulation of PPAR activity during adipogenesis" 2005, Int J Obes (Lond). 29:S13-16.

Gong et al., "LDL receptor-related protein 5 (LRP5) affects bone accrual and eye development." 2001, Cell 107:513-523.

Gregory et al., "The promise of canonical Wnt signaling modulators in enhancing bone repair" 2006, Drug News Perspect 19:445-452.

Krause, et al. "Pharmaceutical modulation of canonical Wnt signaling in multipotent stromal cells for improved osteoinductive therapy." 2010, Proc Natl Acad Sci USA 107(9):4147-4152.

Liu et al., "Canonical Wnts function as potent regulators of osteogenesis by human mesenchymal stem cells" 2009, J Cell Biol 185:67-75.

Liu et al., "Regulating the balance between peroxisome proliferator-activated receptor gamma and beta-catenin signaling during adipogenesis. A glycogen synthase kinase 3beta phosphorylation-defective mutant of beta-catenin inhibits expression of a subset of adipogenic genes." 2004, J Biol Chem 279:45020-45027.

Meijer et al., "GSK-3-selective inhibitors derived from Tyrian purple indirubins." 2003, Chem Biol 10:1255-1266.

Rawadi et al., "BMP-2 controls alkaline phosphatase expression and osteoblast mineralization by a Wnt autocrine loop." 2003, J. Bone Miner Res 18:1842-1853.

Tian et al., "The role of the Wnt-signaling antagonist DKK1 in the development of osteolytic lesions in multiple myeloma." 2003, N. Engl. J. Med. 349:2483-2494.

Van Der Horst et al., "Downregulation of Wnt signaling by increased expression of Dickkopf-1 and -2 is a prerequisite for late-stage osteoblast differentiation of KS483 cells." 2005, J Bone Miner Res 20:1867-1877.

Datta, et al., "In vitro generated extracellular matrix and fluid shear stress synergistically enhance 3D osteoblastic differentiation," PNAS, 103(8):2488-2493 (2006).

Holtorf, et al., "Ectopic bone formation in rate marrow stromal cell/titanium fiber mesh scaffold constructs: Effect of initial cell phenotype," Biomater., 26:6208-6216 (2005).

Pham, et al., "The influence of an in vitro generated bone-like extracellular matrix on osteoblastic gene expression of marrow stromal cells," Biomater., 29:2729-2739 (2008).

Quarles, et al. "Distinct Proliferative and Differentiated Stages of Murine MC3T3-E1 Cells in Culture: An In Vitro Model of Osteoblast Development," 7(6):683-692 (1992).

Shin, et al., "Osteogenic differentiation of rat bone marrow stromal cells cultured on Arg-Gly-Asp modified hydrogels without dexamethasone and β-glycerol phosphate," Biomater., 26:3645-3654 (2005).

Datta, Neha et al., Effect of bone extracellular matrix synthesized in vitro on the osteoblastic differentiation of marrow stromal cells; Biomaterials, 26:971-977 (2005).

Van Den Dolder, Juliette, et al.; Bone formation by rat bone marrow cells cultured on titanium fiber mesh: Effect of in vitro culture time; Journal of Biomedical Materials Research 61(3): 350-358 (2002).

Cool, Simon M., Substrate Induction of Osteogenesis from Marrow-Derived Mesenchymal Precursors; Stem Cells and Development, 14:632-645 (2005).

Sampath, T.K. et al. Dissociative extraction and reconstitution of extracellular matrix components involved in local bone differentiation; Proceedings of the National Academy of Sciences USA, vol. 78, No. 12, Dec. 1981, pp. 7599-7603.

Rodriguez, J. Pablo et al., Mesenchymal Stem Cells from Osteoporotic Patients Produce a Type I Collagen-Deficient Extracellular Matrix Favoring Adipogenic Differentiation; Journal of Cellular Biochemistry 2000 79:557-565.

Dominia, L.V. et al. Isolation and chacteristics of the extracellular matrix of cultured cells; Tsitologila, 30(3): (1988) 299-304 (abstract only).

SIGMA Technical Bulletin, Cultured Cells Acellularization Kit for ECM Preparation (2005), 3 pages.

Allen, Howard J. et al.; Role of Galaptin in Ovarian Carcinoma Adhesion to Extracellular Matrix in Vitro; Journal of Cellular Biochemistry, vol. 43 (1990), pp. 43-57.

Vlodavsky, Israel et al.; Endothelial cell-derived basic fibroblast growth factor: Synthesis and deposition into subendothelial extracellular matrix; Proceedings of the National Academy of Sciences USA, vol. 84, Apr. 1987, pp. 2292-2296.

Badylak, Stephen E., The extracellular matrix as a scaffold for tissue reconstruction; Cell & Development Biology, vol. 13, 2002, pp. 377-383.

Chastain, Sara R. et al., Adhesion of mesenchymal stem cells to polymer scaffolds occurs via distinct ECM ligands and controls their osteogenic differentiation; Journal of Biomedical Materials Research Part A, 78(1): 73-85 (2006).

Gregory, C., et al., How Wnt Signaling Affects Bone Repair by Messenchymal Stem Cells from the Bone Marrow, 2005, Ann. N.Y. Acad. Sci., 1049: 97-106.

International Search Report for PCT Application No. PCT/US2010/028332 Mailed May 20, 2010.

Asahina, I., et al., Human Osteogenic Protein-1 Induces Chondroblastic, Osteoblastic, and/or Adipocytic Differentiation of Clonal Murine Target Cells, 1996, Experimental Cell Research, 222: 38-47.

Austin, T., et al., Blood A Role for the Wnt Gene Family in Hematopoiesis: Expansion of Multilineage Progenitor Cells, 1997, American Society of Hematology, 89: 3624-3635.

Chen, T., et al., Bone Morphogenetic Protein-2b Stimulation of Growth and Osteogenic Phenotypes in Rat Osteoblast-like Cells: Comparison with TGF-β, 1991, Journal of Bone and Mineral Research, 6: 1387-1390.

Colter, D., et al., Rapid expansion of recycling stem cells in cultures of plastic-adherent cells from human bone marrow, 2000, Proceedings of the National Academy of Sciences, 97: 3213-3218.

De Bari, C., et al., Multipotent Mesenchymal Stem Cells From Adult Human Synovial Membrane, 2001, Arthritis & Rheumatism, American College of Rheumatology Published by Wiley-Liss, Inc., 44: 1928-1942.

Deng, W., et al., In Vitro Differentiation of Human Marrow Stromal Cells into Early Progenitors of Neural Cells by Conditions That Increase Intracellular Cyclic AMP, 2001, Biochemical and Biophysical Research Communications, 282: 148-152.

Dexter, T., et al., Haemopoietic Stem Cells and the Problem of Self-renewal, 1984, Blood Cells, 10: 315-322.

Eaves, C., et al., Characterization of Human Hematopoietic Cells with Short-Lived in Vivo Repopulating Activity, 2001, Annals New York Academy of Sciences, 2002, 938: 63-71.

Friedenstein, A., et al., Fibroblast Precursors in Normal and Irradiated Mouse Hematopoietic Organs, 1976, Experimental Hematology 4: 267-274.

Friedenstein, A., et al., Bone marrow osteogenic stem cells: in vitro cultivation and transplantation in diffusion chambers, 1987, Cell and Tissue Kinetics, 20: 263-272.

Fukuda, K., et al., Stem Cells as a Source of Regenerative Cardiomyocytes, 2006, Circulation Research Journal of the American Heart Association, 98: 1002-1013.

(56) References Cited

OTHER PUBLICATIONS

Gregory, C., et al., The Wnt Signaling Inhibitor Dickkopf-1 is Required for Reentry into the Cell Cycle of Human Adult Stem Cells from Bone Marrow, 2003, The Journal of Biological Chemistry, 278: 28067-28078.

Gregory, C., et al., An Alizarin red-based assay of mineralization by adherent cells in culture: comparison with cetylpyridinium chloride extraction, 2004, Analytical Biochemistry, 329: 77-84.

Gregory, C., et al., Adult Bone Marrow Stem/Progenitor Cells (MSCs) Are Preconditioned by Microenvironmental "Niches" in Culture: A Two-Stage Hypothesis for Regulation of MSC Fate, 2005, Science's STKE 294/pe37: 1-4.

Guilak, F., et al., Adipose-derived adult stem cells for cartilage tissue engineering, 2004, Biorheology, 41: 389-399.

Gunn, W., et al., A Crosstalk Between Myeloma Cells and Marrow Stromal Cells Stimulates Production of DKK1 and Interleukin-6: A Potential Role in the Development of Lytic Bone Disease and Tumor Progression in Multiple Myeloma, 2005, Stem Cells 24:986-991.

Hong, J., et al., TAZ, a Transcriptional Modulator of Mesenchymal Stem Cell Differentiation, 2005, Science, 309: 1074-1078.

Kim, S., et al., Neural differentiation potential of peripheral blood- and bone-marrow-derived precursor cells, 2006, Brain Research, 1123: 27-33.

Kopen, G., et al., Marrow stromal cells migrate throughout forebrain and cerebellum, and they differentiate into astrocytes after injection into neonatal mouse brains, 1999, Proceedings of the National Academy of Sciences USA, 96: 10711-10716.

Kota, B., et al., An overview on biological mechanisms of PPARs, 2005, Pharmacological Research, 51: 85-94.

Krampera, M., et al., Mesenchymal stem cells: from biology to clinical use, 2007, Blood Transfus, 5: 120-129.

Kuznetsov, S., et al., Circulating Skeletal Stem Cells, 2001, The Journal of Cell Biology, 153: 1133-1139.

Larson, B., et al., Human Multipotent Stromal Cells Undergo Sharp Transition from Division to Development in Culture, 2008, Stem Cells, 26: 193-201.

Lucki, N., et al, Multiple Roles for Sphingolipids in Steroid Hormone Biosynthesis, 2008, Lipids in Health and Disease, Subcellular Biochemistry, vol. 49: pp. 387-412.

Mareschi, K., et al., Expansion of Mesenchymal Stem Cells Isolated From Pediatric and Adult Donor Bone Marrow, 2006, Journal of Biological Chemistry, 97: 744-754.

Pereira, R., et al., Cultured adherent cells from marrow can serve as long-lasting precursor cells for bone, cartilage, and lung in irradiated mice, 1995, Proceedings of the National Academy of Sciences USA, 92: 4857-4861.

Pittenger, M., et al., Multilineage Potential of Adult Human Mesenchymal Stem Cells, 1999, Science, 284: 143-147.

Prockop, D., Marrow Stromal Cells as Stem Cells for Nonhematopoietic Tissues, 1997, Science 276:711-74.

Rosada, C., et al., The Human Umbilical Cord Blood: A Potential Source for Osteoblast Progenitor Cells, 2003, Calcified Tissue International, 72: 135-142.

Sampath, T., et al., Recombinant Human Osteogenic Protein- 1 (hOP- 1) Induces New Bone Formation in Vivo with a Specific Activity Comparablew ith Natural Bovine Osteogenic Protein and Stimulates Osteoblast Proliferation and Differentiation in Vitro, 1992, The Journal of Biological Chemistry 267: 20352-20362.

Sekiya, I., et al., Expansion of Human Adult Stem Cells from Bone Marrow Stroma: Conditions that Maximize the Yields of Early Progenitors and Evaluate Their Quality, 2002, Stem Cells, 20: 530-541.

Sekiya, I., et al., Adipogenic Differentiation of Human Adult Stem Cells From Bone Marrow Stroma (MSCs), 2004, Journal of Bone and Mineral Research, 19: 256-264.

Seo, M., et al., Differentiation of human adipose stromal cells into hepatic lineage in vitro and in vivo, 2005, Biochemical and Biophysical Research Communications, 328: 258-264.

Takuwa, Y., et al., Bone Morphogenetic Protein-2 Stimulates Alkaline Phosphatase Activity and Collagen Synthesis in Cultured Osteoblastic Cells, MC3T3-E1, 1991, Biochemical and Biophysical Research Communications, 174: 96-101.

Van Den Berg, D., et al., Role of Members of the *Wnt* Gene Family in Human Hematopoiesis, 1998, Blood, 92: 3189-3202.

Wakitani, S., et al., Myogenic Cells Derived from Rat Bone Marrow Mesenchymal Stem Cells Exposed to 5-Azacytidine, 1995, Muscle & Nerve, 18: 1417-1426.

Woodbury, D., et al., Adult Rat and Human Bone Marrow Stromal Cells Differentiate Into Neurons, 2000, Journal of Neuroscience Research, 61: 364-370.

Worgall, T., Regulation of Lipid Metabolism by Sphingolipids, 2008, Subcellular Biochemistry, Lipids in Health and Disease, vol. 49, pp. 371-385.

Wozney, J., et al., Novel Regulators of Bone Formation: Molecular Clones and Activities, 1988, Science, 242: 1528-1534.

Azizi, S., et al., Engraftment and migration of human bone marrow stromal cells implanted in the brains of albino rats—similarities to astrocyte grafts, 1998, Proceedings of the National Academy of Sciences USA, 95: 3908-3913.

Bateman, J., et al., Abnormal type I collagen metabolism by cultured fibroblasts in lethal perinatal osteogenesis imperfecta, 1984, The Journal of Biological Chemistry, 217: 103-115.

Bateman, J., et al., A Frameshift Mutation Results in a Truncated Nonfunctional Carboxyl-terminal Prod(1) Propeptide of Type I Collagen in Osteogenesis Imperfects, 1989, The Journal of Biological Chemistry, 264: 10960-10964.

Clement-Lacroix, P., et al., Lrp5-independent activation of Wnt signaling by lithium chloride increases bone formation and bone mass in mice, 2005, Proceedings of the National Academy of Sciences, 102: 17406-17411.

Gregory, C., et al., Enhanced Engraftment of Mesenchymal Stem Cells in a Cutaneous Wound Model by Culture in Allogenic Species-Specific Serum and Administration in Fibrin Constructs, 2006, Stem Cells, 24: 2232-2243.

Hofstetter, C., et al., Marrow stromal cells form guiding strands in the injured spinal cord and promote recovery, 2002, Proceedings of the National Academy of Sciences USA, 99: 2199-2204.

Horwitz, et al., Transplantability and therapeutic effects of bone marrow-derived mesenchymal cells in children with osteogenesis imperfecta, 1999, Nature America Inc., 5: 309-313.

Horwitz, E., et al., Clinical responses to bone marrow transplantation in children with severe osteogenesis imperfecta, 2001, Blood, 97: 1227-1231.

Jiang, Y., et al., Pluripotency of mesenchymal stem cells derived from adult marrow, 2002, Nature, 418: 41-49.

Jope, R., Lithium and GSK-3: one inhibitor, two inhibitory actions, multiple outcomes, 2003, Trends in Pharmacological Sciences, 24: 441-443.

Khillan, J., et al., Transgenic Mice That Express a Mini-gene Version of the Human Gene for Type I Procollagen (COLIAI) Develop a Phenotype Resembling a Lethal Form of Osteogenesis Imperfects, 1991, The Journal of Biological Chemistry, 266: 23373-23379.

Koc., O., et al., Allogeneic mesenchymal stem cell infusion for treatment of metachromatic leukodystrophy (MLD) and Hurler syndrome (MPSIH), 2002, Bone Marrow Transplantation, 30: 215-222.

Krause, D., et al., Multi-Organ, Multi-Lineage Engraftment by a Single Bone Marrow-Derived Stem Cell, 2001, Cell, 105: 369-377.

Kulkarni, N., et al., Orally Bioavailable GSK-3α/β Dual Inhibitor Increases Markers of Cellular Differentiation In Vitro and Bone Mass In Vivo, 2006, Journal of Bone and Mineral Research, 21: 910-920.

Morvan, F., et al., Deletion of a Single Allele of the Dkk1 Gene Leads to an Increase in Bone Formation and Bone Mass, 2006, Journal of Bone and Mineral Research, 21: 934-945.

Nagaya, N., et al., Transplantation of Mesenchymal Stem Cells Improves Cardiac Function in a Rat Model of Dilated Cardiomyopathy, Circulation: Journal of the American Heart Association, 112: 1128-1135.

(56) References Cited

OTHER PUBLICATIONS

Nedergaard, J., et al., PPARγ in the control of brown adipocyte differentiation, 2005, Biochimica et Biophysica Acta, 1740: 293-304.

Rosen, E., et al., PPARγ is Required for the Differentiation of Adipose Tissue In Vivo and In Vitro, 1999, Molecular Cell, 4: 611-677.

Spees., et al., Internalized Antigens Must Be Removed to Prepare Hypoimmunogenic Mesenchymal Stem Cells for Cell and Gene Therapy, 1989, Molecular Therapy, 9: 747-756.

Aho, A., et al., Incorporation and Clinical Results of Large Allografts of the Extremities and Pelvis, 1994, Clinical Orthopaedics and Related Research, 307: 200-213.

Alexopoulos, L., et al., Developmental and Osteoarthritic Changes in Col6a1 Knockout Mice: The Biomechanics of Collagen VI in the Cartilage Pericellular Matrix, 2009, National Institute of Health Public Access, 60: 771-779.

Aro, H., et al., Clinical Use of Bone Allografts, 1993, Annals of Medicine, 25: 403-412.

Becker, J., et al., Immunohistochemical Distribution of Collagens Types IV, V, and VI and of Pro-collagens Types I and III in Human Alveolar Bone and Dentine, 1986, The Journal of Histochemistry and Cytochemistry, 34: 1417-1429.

Bennett, C., et al., Regulation of Wnt Signaling during Adipogenesis, 2002, The Journal of Biological Chemistry, 277: 30998-31004.

Carraro, G., et al., Similar Sequence-Free Amplification of Human Glyceraldehyde-3-Phosphate Dehydrogenase for Real Time RT-PCR Applications, 2005, Molecular and Cellular Probes, 19: 181-186 (Jun. 2005).

Chou, M., et al., Genomic Organization and Characterization of the Human Type XXI Collagen (COL21A1) Gene, 2002, Genomics, 79: 395-401.

Cuomo, A., et al., Mesenchymal Stem Cell Concentration and Bone Repair: Potential Pitfalls from Bench to Bedside, 2009, The Journal of Bone and Joint Surgery, Incorporated, 91: 1073-1083.

De Boer, H., The History of Bone Grafts, 1988, Clinical Orthopaedics and Related Research, 226: 292-297.

Derubeis, A., et al., Bone Marrow Stromal Cells (BMSCs) in Bone Engineering: Limitations and Recent Advances, 2004, Annals of Biomedical Engineering, 32: 160-165.

Dishowitz, M., et al., Notch Signaling Components are Upregulated during Both Endochondral and Intramembranous Bone Regeneration, 2011, Journal of Orthopaedic Research, 30: 296-303.

Doi, M., et al., Genome-wide Screening by cDNA Microarray of Genes Associated with Matrix Mineralization by Human Mesenchymal Stem Cells in Vitro, 2002, Biochemical and Biophysical Research Communications, 290: 381-390.

Dominici, M., et al., Minimal criteria for defining multipotent mesenchymal stromal cells. The International Society for Cellular Therapy position statement, 2006, Cytotherapy, 8: 315-317.

Edgar. R., et al., Gene Expression Omnibus: NCBI gene expression and hybridization array data repository, 2002, Nucleic Acids Research, 30, 207-210.

Einhorn, T., The Cell and Molecular Biology of Fracture Healing, 1998, Clinical Orthopaedics and Related Research, 355S, S7-S21.

Falster, A., et al., Physical Examination of Caffeine's Effects on the Enamel Surface of First Molar in New-Born Rats, 1992, Archives of Oral Biology, 37: 111-118.

Fitzgerald, J., et al., A new FACIT of the collagen family: COL21A1, 2001, Federation of European Biochemical Societies Lett 505: 275-280.

Gregory, C., et al., Developmental Distribution of Collagen Type XII in Cartilage: Association with Articular Cartilage and the Growth Plate, 2001, Journal of Bone and Mineral Research, 16: 2005-2016.

Gregory, C., et al., Non-hematopoietic bone marrow stem cells: Molecular control of expansion and differentiation, 2005, Experimental Cell Research, 306: 330-335.

Gregory, C., Chapter 2 "Mesenchymal Stem Cells: From Culture to Clinic" of Stem Cell Repair and Regeneration., H. Levicar N., N.A., Gordon, M.Y., Dimarakis, I., Ed., 2008, Imperial College Press, London, vol. 3, pp. 21-43.

Gronthos, S., et al., Integrin Expression and Function on Human Osteoblast-like Cells, 1997, Journal of Bone and Mineral Research, 12: 1189-1197.

Hadjiargyrou, M., et al., Transcriptional Profiling of Bone Regeneration Insight Into the Molecular Complexity of Wound Repair, 2002, The Journal of Biological Chemistry, 277: 30177-30182.

Imamura, Y., et al., The Pro-a3(V) Collagen Chain Complete primary structure, expression domains in adult and developing tissues, and comparison to the structures and expression domains of the other types V and XI procollagen chains, 2000, The Journal of Biological Chemistry, 275, 8749-8759.

Ingham, E., et al., Biological reactions to wear debris in total joint replacement, 2000, Proc Inst Mech Eng H., 214: 21-37.

Iwaki, A., et al., Localization and Quantification of Proliferating Cells During Rat Fracture Repair: Detection of Proliferating Cell Nuclear Antigen by Immunohistochemistry, 1997, The Journal of Biological Chemistry, 12: 96-102.

Kao, S., et al., A Review of Bone Substitutes, 2007, Oral and Maxillofacial Surgery Clinics, 19: 513-521.

Keene, D., et al., Human Bone Contains Type III Collagen, Type VI Collagen, and Fibrillin: Type III Collagen is Present on Specific Fibers That May Mediate Attachment of Tendons, Ligaments, and Periosteum to Calcified Bone Cortex, 1991, The Journal of Histochemistry and Cytochemistry, 39: 59-69.

Kehrel, B., et al., Platelets Deficient in Glycoprotein IIIb Aggregate Normally to Collagens Type I and I11 But Not to Collagen Type V, 1993, Blood, 82: 3364-3370.

Krause, U., et al., Potential of Modulating Wnt Signaling Pathway Toward the Development of Bone Anabolic Agent, 2011, Current Molecular Pharmacology, 5: 1-10.

Krause, U., et al., Assays of Osteogenic Differentiation by Cultured Human Mesenchymal Stem Cells, 2011, Methods in Molecular Biology, 698: 215-230.

Lisignoli, G., et al., Gene Array Profile Identifies Collagen Type XV as a Novel Human Osteoblast-Secreted Matrix Protein, 2009, Journal of Cellular Physiology, 220: 401-409.

Marsell., R., et al., The biology of fracture healing, 2011, Injury, 42: 551-555.

Marsh, D., Concepts of Fracture Union, Delayed Union, and Nonunion, 1998, Clinical Orthopaedics and Related Research, 355S: S22-S30.

Marvulli, D., et al., Spatial and Expression Temporal Changes of Type VI Collagen During Mouse Development; 1996, Developmental Dynamics 206: 447-454.

Mauney, J., et al., Role of Adult Mesenchymal Stem Cells in Bone Tissue-Engineering Applications: Current Status and Future Prospects, 2005, Tissue Engineering, 11: 787-802.

Moldes, M., et al., Peroxisome-proliferator-activated receptor γ suppresses Wnt/β-catenin signalling during adipogenesis, 2003, Biochem J. 376: 607-613.

Morris, N., et al., Developmentally Regulated Alternative Splicing of the α1 (XI) Collagen Chain: Spatial and Temporal Segregation of Isoforms in the Cartilage of Fetal Rat Long Bones, 2000, The Journal of Histochemistry and Cytochemistry, 48: 725-741.

Nemoto, T., et al., Differential induction of collagens by mechanical stress in human periodontal ligament cells, 2010, Archives of Oral Biology, 55: 981-97.

Niyibizi, C., et al., Identification of the cartilage al(X1) chain in type V collagen from bovine bone, 1989, FEBS Letters, 242: 314-318.

Ode, A., et al., Toward biomimetic materials in bone regeneration: Functional behavior of mesenchymal stem cells on a broad spectrum of extracellular matrix components, 2010, The Journal of Biomedical Materials Research, 95A: 1114-1124.

Owen, M., et al., Stromal stem cells: marrow-derived osteogenic precursors, 1988, Cell and Molecular Biology of Vertebrate Hard Tissues, Ciba Foundation Symposium, 136: 42-60.

Pattyn, F., et al., RTPrimerDB: the Real-Time PCR primer and probe database, 2003, Nucleic Acids Research, 31: 122-123.

(56) References Cited

OTHER PUBLICATIONS

Pattyn, F., et al., RTPrimerDB: the Real-Time PCR primer and probe database, major update 2006, Nucleic Acids Research, 34: D684-D688.

Phinney, D., et al., Plastic Adherent Stromal Cells From the Bone Marrow of Commonly Used Strains of Inbred Mice: Variations in Yield, Growth, and Differentiation, 1999, Journal of Cellular Biochemistry, 72: 570-585.

Phinney, D., Biochemical Heterogeneity of Mesenchymal Stem Cell Populations Clues to their Therapeutic Efficacy, 2007, Cell Cycle, 6: 2884-2289.

Phinney, D., et al., Donor Variation in the Growth Properties and Osteogenic Potential of Human Marrow Stromal Cells, 1999, Journal of Cellular Biochemistry, 75: 424-436.

Phinney, D., et al., Concise Review: Mesenchymal Stem/Multipotent Stromal Cells: The State of Transdifferentiation and Modes of Tissue Repair—Current Views, 2007, Stem Cells, 25: 2896-2902.

Pinnell, S., Regulation of Collagen Biosynthesis by Ascorbic Acid: A Review, 1985, The Yale Journal of Biology and Medicine, 58: 553-559.

Rihn, J., et al., Graft Options in Posterolateral and Posterior Interbody Lumbar Fusion, 2010, Spine, 35: 1629-1639.

Roulet, M., et al., A comprehensive study of the spatial and temporal expression of the col5a1 gene in mouse embryos: a clue for understanding collagen V function in developing connective tissues, 2007, Cell Tissue Res 327, 323-332.

Rubery, P., Enhancing Allograft Bone Healing Through Gene Therapy, 2010, Spine, 35: 1640-1647.

Schindeler, A., et al., Seminars in Cell & Developmental Biology, 2008, Seminars in Cell & Developmental Biology, 19: 423.

Schmidt, A., et al., TGF-β1 generates a specific multicomponent extracellular matrix in human coronary SMC, 2006, European Journal of Clinical Investigation, 36: 473-482.

Schwarz, E., et al., Bone implant interface, osteolysis and potential therapies, 2004, J Musculoskel Neuron Interact, 4: 390-392.

Sekiya, I., et al., BMP-6 Enhances Chondrogenesis in a Subpopulation of Human Marrow Stromal Cells, 2001, Biochemical and Biophysical Research Communications, 284: 411-418.

Sekiya, I., et al., In vitro cartilage formation by human adult stem cells from bone marrow stroma defines the sequence of cellular and molecular events during chondrogenesis, 2002, Proceedings of the National Academy of Sciences USA, 99: 4397-4402.

Shapiro, F., Bone Development and Its Relation to Fracture Repair. The Role of Mesenchymal Osteoblasts and Surface Osteobla, 2008, European Cells and Materials, 15: 53-76.

Shegarfi, H., et al., Review article: Bone transplantation and immune response, 2009, Journal of Orthopaedic Surgery, 17: 206-211.

Sugrue, S., et al., Immunoidentification of Type XII Collagen in Embryonic Tissues, 1989, The Journal of Cell Biology, 109: 939-945.

Walchli, C., et al., Tissue-specific expression of the fibril-associated collagens XII and XIV, 1994, Journal of Cell Science, 107: 669-681.

Yamaguchi, K., et al., Pro-a3(V) collagen chain is expressed in bone and its basic N-terminal peptide adheres to osteosarcoma cells, 2005, Matrix Biology, 24: 283-294.

Yamazaki, M., et al., Spatial and Temporal Expression of Fibril-Forming Minor Collagen Genes (Types V and XI) during Fracture Healing, 1997, Journal of Orthopaedic Research, 1997, 757-764.

Issack et al., Role of Wnt Signaling in Bone Remodeling and Repair; Hospital for Special Surgical Journal (2008) 4: 66-70, published online Dec. 8, 2007.

Sikavitsas, et al. Pre-culture period of mesenchymal stem cells in osteogenic media influences their in vivo bone forming potential, Journal of Biomedical Materials Research Part A, Published Jan. 31, 2007, vol. 82, pp. 129-138.

Jokoby, William B., and Pastan, Ira H., Cell Culture, Methods in Enzymology, vol. LVIII, published by Academic Press, Inc., pp. 62-72.

Gregory, et al. dkk-1-derived Synthetic Peptides and Lithium Choloride for the Control and Recovery of Adult Stem Cells from Bone Marrow; published Jun. 4, 2004; Journal of Biological Chemistry, vol. 280, No. 3, pp. 2309-2323.

Gregory, C. A., Prockop, D. J., Fundamentals of Culture and Characterization of Mesenchymal Stem/Progenitor Cells (MSCs) from Bone Marrow Stroma; Culture of Human Stem Cells, 2007, pp. 207-232.

Hak, D. J., Removal of Broken Hardware, Journal of the American Academy of Orthopaedic Surgeons, vol. 16, No. 2, Feb. 2008, pp. 113-120.

Rosemont, I. L., Chapter 6 from United States Bone and Joint Decade: The burden of musculoskeletal diseases and musculoskeletal injuries; American Academy of Orthopedic Surgeons, 2008, pp. 123-162.

Farrell, E., et al., "A collagen-glycosaminoglycan scaffold supports adult rat mesenchymal stem cell differentiation along osteogenic and chondrogenic routes," Tissue Engineering, 12(3):459-468 (2006).

Marston, WA, et al., "The efficacy and safety of Dermagraft in improving the healing of chronic diabetic foot ulcers," Diabetes Care, 26:1701-1705 (2003).

Datta, N, et al., "Effect of bone extracellular matrix synthesized in vitro on the osteoblastic differentiation of marrow stromal cells," Biomaterials, 26:971-977 (2005).

* cited by examiner a.
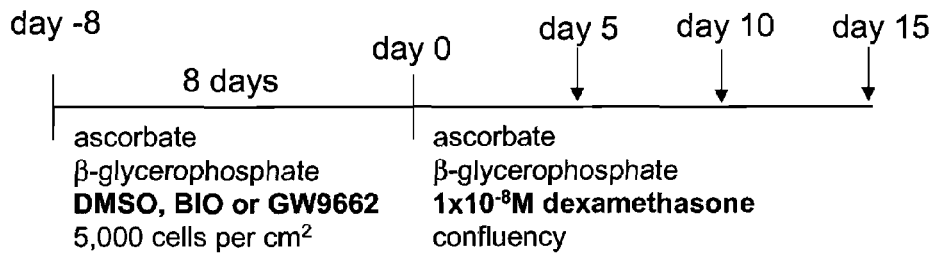
b.
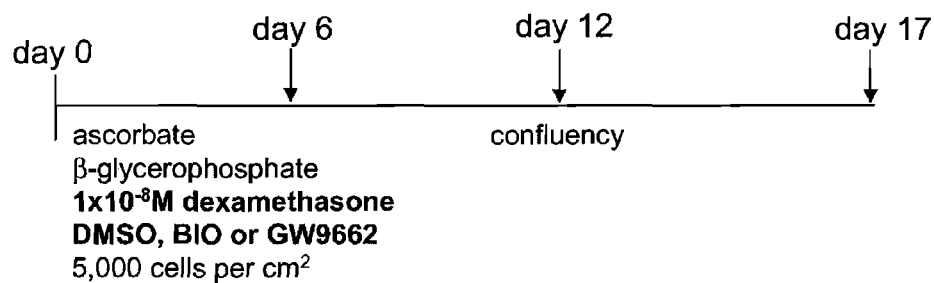
c.
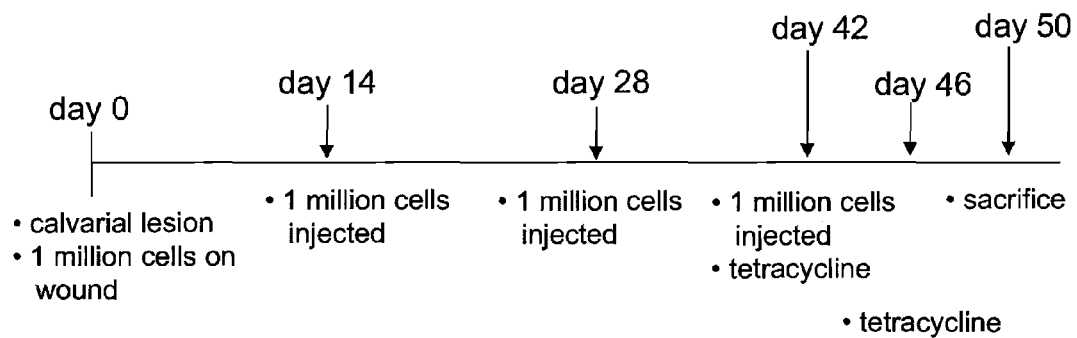
Figure 12

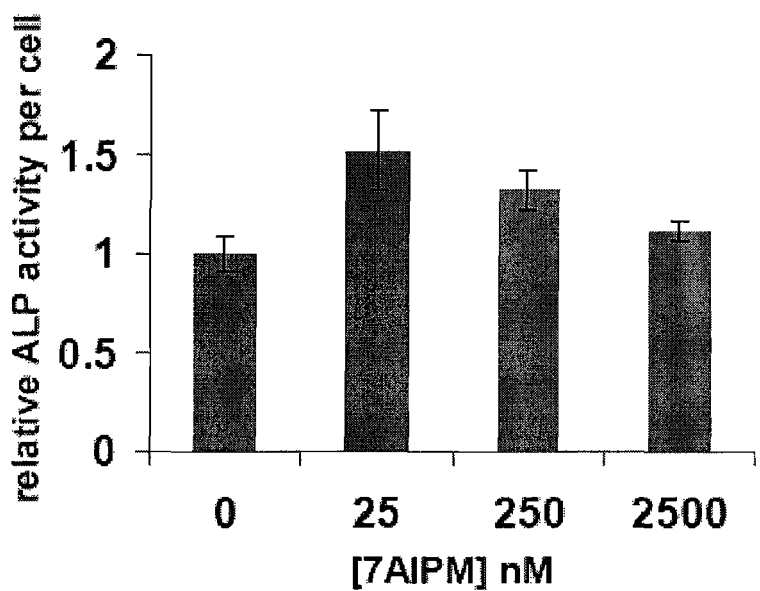
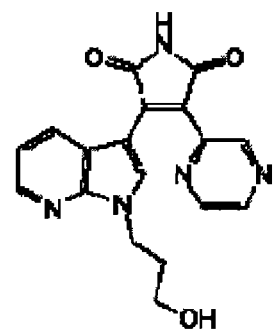
Figure 20

| Function | Score |
|---|---|
| Membrane part | 27.5164 |
| Intrinsic to membrane | 26.0127 |
| Integral to membrane | 23.6473 |
| RNA binding | 20.2434 |
| RNA processing | 19.4775 |
| RNA metabolic process | 18.9374 |
| mRNA processing | 18.3935 |
| Membrane | 17.8623 |
| Receptor activity | 16.5981 |
| mRNA metabolic process | 16.1985 |
| Nuclear body | 16.0694 |
| Intracellular part | 15.3647 |
| Transmembrane receptor activity | 15.2685 |
| Regulation of Ras GTPase activity | 15.2184 |
| Regulation of GTPase activity | 14.6535 |
| Nucleoplasm part | 14.2069 |
| Nuclear part | 13.7130 |
| Intracellular organelle | 13.5684 |
| RNA splicing | 13.4278 |
| Signal transducer activity | 13.3653 |
| Molecular transducer activity | 13.3653 |
| Nuclear mRNA splicing, via spliceosome | 13.3446 |
| Regulation of ARF GTPase activity | 13.2798 |
| Nucleotide binding | 13.1939 |
| Collagen | 13.1052 |
| GTPase activator activity | 12.9198 |
| ARF GTPase activator activity | 12.7744 |
| G protein coupled receptor protein signaling pathway | 12.0761 |
| Protein localization | 12.0587 |
| GTPase regulator activity | 11.8750 |
| Response to stimulus | 11.8577 |
| G protein coupled receptor activity | 11.7330 |
| Macromolecule localization | 11.4025 |
| Cellular macromolecule metabolic process | 11.3837 |
| Nuclear speck | 11.3583 |
| Nucleus | 11.3502 |
| Ras GTPase activator activity | 11.0715 |
| Plasma membrane | 11.0066 |
| Immune response | 10.9736 |
| Cytoplasm | 10.8964 |
| Muscle thin filament tropomyosin | 10.7406 |
| Protein binding | 10.7210 |
| Intrinsic to plasma membrane | 10.7024 |
| Protein farnesyltransferase activity | 10.3374 |
| Protein amino acid farnesylation | 10.3374 |
| Hemidesmosome | 10.3374 |
| Integral to plasma membrane | 10.3207 |
| Cellular protein metabolic process | 10.1287 |
| Biopolymer metabolic process | 9.86304 |
| Rhodopsin-like receptor activity | 9.82835 |
| Extracellular region | 9.67791 |
| Intracellular membrane-bounded organelle | 9.62580 |
| Macromolecule metabolic process | 9.45201 |
| Protein modification process | 9.20919 |
| Plasma membrane part | 9.08948 |
| Intracellular transport | 9.01389 |
| Ubiquitin-protein ligase activity | 8.89770 |
| Acid-amino acid ligase activity | 8.72389 |
| Zinc ion binding | 8.68187 |
| Small conjugating protein ligase activity | 8.47253 |
| Neuromuscular junction development | 8.26452 |
| Cellular_component | 8.15432 |

Figure 21A

| Function | Score |
|---|---|
| Transmembrane transporter activity | 8.14914 |
| NADPH:quinone reductase activity | 8.11148 |
| Polytene chromosome chromocenter | 8.11148 |
| Negative regulation of Rho protein signal transduction | 8.11148 |
| Establishment of localization in cell | 8.01233 |
| ATP-dependent helicase activity | 7.89262 |
| Binding | 7.74701 |
| Transporter activity | 7.71191 |
| Heterogeneous nuclear ribonucleoprotein complex | 7.57409 |
| Golgi to endosome transport | 7.36078 |
| Wnt receptor signaling pathway through beta-catenin | 7.36078 |
| Nucleic acid binding | 7.21703 |
| Posttranslational protein modification | 7.18282 |
| Regulation of small GTPase mediated signal transduction | 7.13642 |
| Metal ion transport | 7.13251 |
| Ligase activity, forming carbon-nitrogen bonds | 7.00821 |
| Localization | 6.80309 |
| Mediator complex | 6.78123 |
| Transition metal ion binding | 6.77774 |
| Ubiquitin-dependent protein catabolic process | 6.74139 |
| Extracellular space | 6.64369 |
| Double-stranded DNA binding | 6.62313 |
| Polynucleotide adenylyltransferase activity | 6.61480 |
| Farnesyltranstransferase activity | 6.61480 |
| Receptor tyrosine kinase binding | 6.61480 |
| Beta-N-acetylhexosaminidase activity | 6.61480 |
| Vesicle | 6.61480 |
| Organelle | 6.61480 |
| Protein import into mitochondrial matrix | 6.61480 |
| Fibrillar collagen | 6.60614 |
| Camera-type eye morphogenesis | 6.60614 |
| Modification-dependent protein catabolic process | 6.54899 |
| Multicellular organismal process | 6.49879 |
| Channel activity | 6.48427 |

Enrichment scores are derived from $P$ values ($10^{-enrichment\ score} = P$ value against the probability that a given gene clustered based on chance alone).

Figure 21B

| Protein | Gene | Accession No. | Fold changes | | | | Major location/function |
|---|---|---|---|---|---|---|---|
| | | | BIO200 | BIO800 | GW1 | GW10 | |
| *Collagen Ia1* | *COL1A1* | 217430_x_at | 2.75 | 2.79 | 2 | 3 | Abundant in bone |
| *Collagen Ia1* | *COL1A1* | 202311_s_at | 2.36 | 2.2 | 2.05 | 2.25 | |
| *Collagen Ia2* | *COL1A2* | 225664_at | 2.38 | 1.88 | 1.79 | 3.93 | Abundant in bone |
| *Collagen IIIa1* | *COL3A1* | 232458_at | 3.12 | 1.22 | 10.4 | 2.8 | Present in bone |
| Collagen IVa5 | COL4A5 | 213110_s_at | *−2.05* | *−2.65* | *−1.84* | *−1.29* | Low/absent in bone |
| *Collagen Va3* | *COL5A3* | 52255_s_at | 1.91 | 1.12 | 1.52 | 3.34 | Present/low in bone |
| *Collagen VI a1* | *COL6A1* | 212091_s_at | 1.92 | 1.66 | 1.85 | 3.23 | Present in bone |
| *Collagen VI a1* | *COL6A1* | 212940_s_at | 2.05 | 1.66 | 1.14 | 2.99 | |
| *Collagen VI a2* | *COL6A2* | 209156_s_at | 1.96 | 1.91 | 2.38 | 2.71 | Present in bone |
| *Collagen VIIIa1* | *COL8A1* | 221152_at | 1.42 | 1.12 | 4.07 | 1.57 | Low in bone |
| *Collagen VIIIa2* | *COL8A2* | 52651_at | 2.12 | 2.43 | 1.14 | 1.24 | Low in bone |
| *Collagen Xa1* | *COL10A1* | 217428_s_at | 1.65 | 2.18 | 1.37 | 1.47 | Present in mature bone |
| Collagen XIa1 | COL11A1 | 229271_x_at | −1.54 | −1.02 | 2.28 | 5.01 | Cartilage restricted |
| Collagen XIa1 | COL11A1 | 37982_at | *−2.2* | *−3.29* | 5.57 | 4.02 | |
| *Collagen XIIa1* | *COL12A1* | 231766_s_at | 2.38 | 1.88 | 1.79 | 3.93 | Present in bone |
| *Collagen XIIa1* | *COL12A1* | 225664_at | 1.5 | 1.29 | 1.23 | 2.79 | |
| *Collagen XIIa1* | *COL12A1* | 231879_at | 2.11 | 1.62 | 1.13 | 4 | |
| Collagen XIVa1 | COL14A1 | 212865_s_at | *−3.47* | *−4.59* | *−2.28* | 2.2 | Marrow stroma |
| *Collagen XVa1* | *COL15A1* | 203477_at | *−1.83* | *−2.25* | 2.03 | 2.04 | Some osteoblasts |
| Aggrecan | ACAN | 217161_x_at | 1.09 | 1.2 | 1.3 | 2.7 | Cartilage restricted |
| Fibronectin | FN1 | 1558199_at | 1.88 | 1.87 | 7.29 | 2.6 | Synthesizing bone |

Bone-related collagens are italicized in the first two columns; high abundance bone-related collagens are bold. Significant fold increases are presented in bold in columns 4–6; significant fold decreases are presented in italic.

Figure 22

| Function | Score |
|---|---|
| Highly down-regulated in BIO-treated MSCs, moderately down-regulated in GW9662-treated MSCs. | |
| Thrombin receptor activity | 28.0695 |
| Trans-1,2-dihydrobenzene-1,2-diol dehydrogenase activity | 28.0695 |
| 3-Alpha-hydroxysteroid dehydrogenase (A-specific) activity | 22.5322 |
| Prostanoid metabolic process | 17.3850 |
| Prostaglandin metabolic process | 17.3850 |
| Phospholipid scrambling | 14.8662 |
| Phospholipid scramblase activity | 14.8662 |
| Bile acid binding | 14.8662 |
| Acetylgalactosaminyltransferase activity | 13.6365 |
| Platelet-derived growth factor receptor activity | 12.6591 |
| Response to dsRNA | 12.6591 |
| Prostaglandin E receptor activity | 12.6591 |
| Indole and derivative metabolic process | 12.6591 |
| Indole derivative metabolic process | 12.6591 |
| Regulation of ossification | 12.3625 |
| Carboxylic acid binding | 10.9963 |
| 3',5'-Cyclic-nucleotide phosphodiesterase activity | 10.7854 |
| Steroid dehydrogenase activity, acting on the CH-OH group of donors, NAD or NADP as acceptor | 10.3329 |
| Cyclic-nucleotide phosphodiesterase activity | 10.3329 |
| Adenylate kinase activity | 9.69717 |
| Integrin complex | 8.79613 |
| Highly down-regulated in GW9662 treated MSCs, moderately down-regulated in BIO-treated MSCs | |
| Sphingomyelin biosynthetic process | 21.4244 |
| Extracellular region | 18.6676 |
| Sphingomyelin synthase activity | 16.4884 |
| Ceramide cholinephosphotransferase activity | 16.4884 |
| Cytoplasmic part | 16.1805 |
| Stearoyl-CoA 9-desaturase activity | 12.2139 |
| Intracellular part | 11.1996 |
| Intracellular organelle part | 10.5470 |
| Y-form DNA binding | 9.62809 |
| Transcription, RNA-dependent | 9.62809 |
| Negative regulation of retroviral genome replication | 9.62809 |
| Ubiquitin-dependent protein catabolic process | 9.59400 |
| Endoplasmic reticulum | 9.49858 |
| Modification-dependent protein catabolic process | 9.35670 |
| Golgi-associated vesicle | 8.89415 |
| Signal transduction | 8.86723 |
| Extracellular region part | 8.62576 |
| Nucleosome assembly | 8.59450 |
| Protein import | 8.48681 |
| Nucleosome | 8.18840 |
| Regulation of defense response to virus by host | 8.02484 |
| Extracellular space | 7.99858 |

Enrichment scores are derived from $P$ values ($10^{-enrichment\ score} = P$ value against the probability that a given gene clustered based on chance alone).

Figure 23

| Function | Score |
|---|---|
| Positive regulation of epidermal growth factor receptor activity | 83.2622 |
| Neutrophil chemotaxis | 79.0106 |
| G protein-coupled receptor binding | 68.7486 |
| Chemokine activity | 67.9314 |
| Fever | 65.5733 |
| Chemokine receptor binding | 65.4490 |
| Regulation of protein secretion | 58.0544 |
| Epidermal growth factor receptor activating ligand activity | 52.4821 |
| Leukocyte chemotaxis | 50.0283 |
| Epidermal growth factor receptor binding | 48.2312 |
| Response to wounding | 44.179 |
| Respiratory burst | 43.7386 |
| Heat generation | 43.7386 |
| Positive regulation of phosphorylation | 43.7127 |
| Positive regulation of cell cycle | 42.6954 |
| Leukocyte migration | 40.3008 |
| Inflammatory response | 40.1391 |
| Positive regulation of phosphate metabolic process | 38.4481 |
| Regulation of interleukin-6 biosynthetic process | 38.3896 |
| Plasminogen activator activity | 37.4817 |
| Positive regulation of interleukin-6 biosynthetic process | 37.4817 |
| Macrophage chemotaxis | 37.4817 |
| Lymphocyte chemotaxis | 37.4817 |
| Induction of programmed cell death in response to chemical stimulus | 33.7693 |
| Regulation of short-term neuronal synaptic plasticity | 33.7693 |

Enrichment scores are derived from $P$ values ($10^{-enrichment\ score} = P$ value against the probability that a given gene clustered based on chance alone).

Figure 24

| Protein | Gene | Accession no. | Fold changes | | | | Major known function | Ligand confirmed |
|---|---|---|---|---|---|---|---|---|
| | | | BIO200 | BIO800 | GW1 | GW10 | | |
| Interleukin 1A | IL-1A | 210118_s_at | 2.53 | 2.80 | −2.87 | −2.15 | Proinflammatory | n.d. |
| Interleukin 1B | IL-1B | 205067_at | 2.07 | 2.42 | −3.15 | −4.40 | Proinflammatory | Yes |
| Interleukin 8 | IL-8 | 20842_s_at | 2.8 | 6.38 | −5.23 | −6.70 | Proinflammatory | Yes |
| Interleukin 8 | IL-8 | 202859_s_at | 1.56 | 2.99 | −6.48 | −18.97 | Proinflammatory | Yes |
| CXC ligand 1 (GROα) | CXCL1 | 204470_at | 1.58 | 2.45 | −5.91 | −8.17 | Neutrophil attractant | Yes |
| CXC ligand 2 | CXCL2 | 209774_x_at | −1.21 | 1.31 | −4.49 | −5.61 | Leukocyte attractant | No |
| CXC ligand 5 (ENA-78) | CXCL5 | 214974_x_at | 1.03 | 3.6 | −1.08 | −1.16 | Neutrophil attractant | Yes |
| CXC ligand 6 (GCP-2) | CXCL6 | 206336_at | −1.25 | 1.49 | −9.13 | −5.12 | Neutrophil attractant | Yes |
| Interleukin 7 | IL-7 | 206693_at | −3.3 | −3.19 | −3.38 | −3.20 | Lymphoid mitogen | n.d. |

Significant fold increases are presented in bold in columns 4–6; significant fold decreases are presented in italic. n.d., not detected.

Figure 25

| Ligand | DMSO* | GW1.0* | GW10.0* | BIO200 | BIO800 |
| --- | --- | --- | --- | --- | --- |
| IL-1 beta[†] | $4.5 \times 10^{-5}$ | $4.5 \times 10^{-6}$ | BDL | NC | NC |
| IL-8[‡] | $1.6 \times 10^{-5}$ | $3.5 \times 10^{-6}$ | $6.8 \times 10^{-9}$ | NC | NC |
| CXCL1[§] | 0.01 | 0.001 | $7.2 \times 10^{-6}$ | NC | NC |
| CXCL2[†] | 0.01 | 0.0016 | $5.8 \times 10^{-4}$ | NC | NC |
| CXCL6[‡] | 0.07 | 0.005 | BDL | NC | NC |

BDL, below detectable levels; NC, no significant change.
*Nanograms secreted per cell per 48 h.
[†]ELISA intra-assay variation <7.5%.
[‡]ELISA intra-assay variation <5%.
[§]ELISA intra-assay variation <10%.

Figure 26

|  | Animal number | | | | | |
| --- | --- | --- | --- | --- | --- | --- |
| Treatment | 1 | 2 | 3 | Mean | SD | P (Student's t test) |
| DMSO | 235 | 141 | 206 | 194 | 48.13 | Versus DMSO |
| BIO200 | 12 | 52 | 0 | 21.33 | 27.23 | 0.0057 |
| BIO800 | 11 | 0 | 31 | 14 | 15.72 | 0.003 |
| GW1.0 | 362 | 188 | 247 | 260.67 | 90.47 | ns |
| GW10.0 | 341 | 215 | 232 | 262.67 | 68.36 | ns | ns, not significant.

Figure 27

COMPOSITIONS OF MESENCHYMAL STEM CELLS TO REGENERATE BONE

CROSS-REFERENCE TO RELATED APPLICATIONS

This application is claims priority under 35 U.S.C. §119(e) to U.S. Provisional Application No. 61/210,764, filed Mar. 23, 2009, which is hereby incorporated by reference in its entirely herein.

STATEMENT REGARDING FEDERALLY SPONSORED RESEARCH OR DEVELOPMENT

This invention was made, in part, using funds obtained from the U.S. Government (National Institutes of Health Grant Nos. R21DK071780 and P20RR020152-01), and the U.S. Government therefore has certain rights in this invention.

BACKGROUND OF THE INVENTION

In vitro and in vivo hMSCs can differentiate into osteoblasts, adipocytes, and chondrocytes (Friedenstein et al., 1976, Exp Hematol 4:267-274; Friedenstein et al., 1987, Cells Tiss Kin 20:263-272; Pereira et al., 1995, Proc Natl Acad Sci 92:4857-4861; Pittenger et al., 1999, Science 284:143-147; Sekiya et al., 2002, Proc Natl Acad Sci USA 99:4397-4402; Sekiya et al., 2004, J Bone Miner Res 19:256-264) but they also adopt a stromal role, by providing extra cellular matrix components, cytokines, and growth factors for paracrine tissue support (Dexter et al., 1984 Blood Cells 10:315-39; Austin et al., 1997 Blood 89:3624-3635; VanDenBerg et al. 1998, Blood 92:3189-3202). As the presumptive precursors of osteoblasts, hMSCs and related cell lines provide a convenient cell culture model for the study of osteogenic tissue repair in an experimentally accessible system (Gregory et al., 2004, Anal Biochem 329:77-84). Early studies, employing cultures of osteogenic progenitors have yielded a wealth of information describing the molecular events that modulate osteogenic differentiation. A critical finding of these studies is that positive signaling by the canonical wingless (Wnt) pathway is essential for differentiation into osteoblasts (Bain et al., 2003, Biochem Biophys Res Commun 301:84-91; Rawadi et al., 2003, J. Bone Miner Res 18:1842-1853; Gregory et al., 2006, Drug News Pers 19:445-452). In the canonical Wnt signaling pathway, secreted Wnt ligands bind to the receptor frizzled (Frz) and the co-receptor lipoprotein-related protein 5 and 6 (LRP-5/6) on the target cell. Activation of Frz recruits the cytoplasmic bridging molecule, disheveled (Dsh), so as to inhibit the action of glycogen-synthetase-kinase-3β (GSK3β). Inhibition of GSK3β decreases phosphorylation of β-catenin, preventing its degradation by the proteosome. Stabilized β-catenin acts on the nucleus by activating T-cell factor/lymphoid enhancing factor mediated transcription of target genes that elicit a variety of effects including induction of differentiation and in some cases, proliferation. Canonical Wnt signaling is tightly regulated by a combination of positive induction through the binding of the Wnt ligand and negative regulation through numerous mechanisms including the secreted glycoprotein dickkopf-1 (Dkk-1) (Tian et al., 2003, N. Engl. J. Med. 349:2483-2494).

The clinical significance of Wnt signaling in osteogenesis has been highlighted by reports that mutations in LRP5 that prevent Dkk-1 binding, cause abnormally high bone density (Boyden et al., 2002, N Eng J Med 346:1513-1521) and mutations that render LRP5 functionally null cause a form of osteoporosis (Gong et al., 2001, Cell 107:513-523).

MSCs from human bone marrow have the capacity to regenerate bone when administered at the site of injury. However, their efficacy is limited because the cultures of MSCs employed are frequently functionally heterogeneous. Therefore a proportion of the administered cells do not contribute to repair of the bone tissue.

In many cases, serious bone trauma does not heal because the damage is too severe to permit the normal process of repair. Serious non-healing bone injuries are usually treated by one or a combination of the following techniques; prosthetic implantation, e.g. plates, pins, or screws, bone graft using autologus explantation, then implantation at the site of injury, or bone morphogenic protein (BMP) implantation. Prosthetic implants are generally straightforward and can be effective, but the body cannot maintain the material as it does with bone tissue. Therefore, weight bearing prosthetics are susceptible to wear. Furthermore, in some cases bone degradation occurs at the site and the implants can be rejected. Bone autografts have the obvious drawback of requiring donor material, limiting the size of the implant. BMPs can accelerate the inherent healing capacity of bone, but if the bone is destroyed, BMPs cannot repair the injury.

There is a need in the art for novel therapeutic formulations of MSCs. Specifically, the prior art is deficient in compositions of MSCs effective to stimulate osteogenesis at a site of bone degeneration or bone injury. The present invention fulfills this long-standing need and desire in the art.

SUMMARY OF THE INVENTION

The invention provides a composition comprising a mesenchymal stem cell (MSC) pre-cultured in the presence of an agent that activates canonical Wnt signaling therein.

In one embodiment, the composition further comprises a biocompatible lattice. In one embodiment, the biocompatible lattice is a clotted plasma.

In one embodiment, the agent that activates canonical Wnt signaling therein is an inhibitor of glycogen synthetase kinase-3-beta. In one embodiment, the inhibitor of glycogen synthetase kinase-3-beta selected from the group consisting of bromo-indirubin-oxime, bromo-indirubin-3'-mono-oxide (BIO), 7-azaindolyl-pyrazinylmaleimide (7AIPM), and a combination thereof.

In one embodiment, the agent that activates canonical Wnt signaling therein is an inhibitor of peroxisome proliferator-activated receptor gamma. In one embodiment, the inhibitor of peroxisome proliferator-activated receptor gamma is 2-chloro-5-nitro-N-phenylbenzamide (GW9662).

In one embodiment, the pre-cultured MSC exhibits at least one characteristic of a bone cell.

In one embodiment, pre-cultured MSC is partially differentiated into a primitive osteoblast.

The invention also provides a composition comprising a mesenchymal stem cell (MSC) and an agent that activates canonical Wnt signaling therein.

The invention provides a method of treating bone degeneration or injury associated with a pathophysiological condition in a mammal. The method comprises administering to the mammal in need thereof an effective amount of a composition comprising a mesenchymal stem cell (MSC) pre-cultured in the presence of an agent that activates canonical Wnt signaling therein, thereby treating the bone degeneration or injury in the mammal. Preferably, the mammal is a human.

In one embodiment, the method further comprises readministering a composition comprising a mesenchymal stem cell (MSC) pre-cultured in the presence of an agent that activates canonical Wnt signaling therein.

In one embodiment, the composition comprising a mesenchymal stem cell (MSC) pre-cultured in the presence of an agent that activates canonical Wnt signaling therein is readministered about every two weeks.

In one embodiment, the step of administering the composition comprising a mesenchymal stem cell (MSC) pre-cultured in the presence of an agent that activates canonical Wnt signaling therein comprises injecting or implanting the cell into the site of bone degeneration or injury.

In one embodiment, the bone degeneration or injury is associated with a cancer. In one embodiment, the cancer is an osteosarcoma, multiple myeloma or a breast or prostate cancer metastasizing to the bone.

In one embodiment, the bone degeneration or injury is associated with osteoporosis, osteogenesis imperfecta, or severe cranial injury. In one embodiment, the bone injury is a bone fracture or break.

The present invention provides a method of accelerating repair of a skeletal injury in a mammal. The method comprises directly contacting the site of the skeletal injury with an effective amount of a composition comprising a mesenchymal stem cell (MSC) pre-cultured in the presence of an agent that activates canonical Wnt signaling therein thereby accelerating bone repair. Preferably, the mammal is human.

The invention provides a mesenchymal stem cell (MSC) pre-cultured in the presence of an agent that activates canonical Wnt signaling therein, wherein the MSC exhibits an elevated osteogenic characteristic compared to an otherwise identical MSC not pre-cultured in the presence of said agent.

The invention provides an MSC-derived lattice comprising extracelluar matrix secreted from an MSC pre-cultured in the presence of an agent that activates canonical Wnt signaling therein that has been induced to differentiate to exhibit at least one characteristic of a bone cell.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown.

FIGS. 1A and 1B, is a series of illustrations depicting the effect of Dkk-1 (FIG. 1A) or the PPARγ agonist, troglitazone (FIG. 1B) on alkaline phosphatase (ALP) activity and osteoprotegerin (OPG secretion. ALP activity was visualized by staining and measured by colorimetric assay. OPG was measured from the medium by ELISA. Values were normalized to cell number. Data represent means±SD (n=6), p<0.05*, p<0.01**.

FIGS. 2A through 2C, is a series of illustrations depicting the effects of β-glycerophosphate and ascorbic acid on osteogenesis alone and when provided with a bone morphogenic protein, dexamethasone, or various PPARγ agonists. FIG. 2A, which includes 3 bar graphs, depicts ALP activity from monolayers of hMSCs obtained from 3 different donors (A, B, and C) after being exposed to complete media (CCM, see none), CCM with osteogenic base media (OBM) supplemented with 5 mM β-glycerophosphate and 50 $\mu g \cdot mL^{-1}$ ascorbic acid (see osteo), OBM supplemented with various concentrations (in $ng \cdot mL^{-1}$) of a bone morphogenic protein 2 (see BMP100 or BMP200), or dexamethasone ($10^{-8}$ M, see dex). Note that the ALP levels are substantially raised by OBM treatment and can be improved further by high concentrations of BMP100 or BMP200 (n=3). FIG. 2B depicts the effect of 50 μM of various PPARγ agonists on ALP activity measured by colorimetric assay. All values were normalized to cell number. Data are expressed as means with standard deviations (n=6). Pioglitazone (pio), rosiglitazone (ros), ciglitazone (cig), and troglitazone (trog) were used. FIG. 2C includes two images demonstrating that in the presence of high concentrations of PPARγ agonists, osteogenic cultures of hMSCs initiate adipogenesis rather than osteogenesis. After 20 days of differentiation in OBM containing $10^{-8}$ M dex and 10 μM troglitazone, cultures show Oil Red O-positive lipid islands (left) and only weak mineralization (Alizarin red S [ARS] staining, right).

FIGS. 3A through 3D, is a series of images depicting the effects of BIO and GW. FIG. 3A demonstrates that BIO and GW are predicted to up-regulate Wnt signaling by direct inhibition of GSK3β or by ablating PPARγ mediated negative crosstalk respectively. FIG. 3B is an image of a fluorescent microscopy of hMSCs with counterstained nuclei (pico-green, left) or cy-3 labeled anti-β-catenin stained nuclei (right). FIG. 3C depicts immunoblots of cytosolic GSK3β (C GSK3β), nuclear β-catenin (N β-cat) and nuclear PPARγ (N-PPARγ) on extracts of hMSCs treated with BIO or GW. Blots were normalized for cytosolic proteins with GAPDH (C GAPDH) and for nuclear proteins by silver stain. FIG. 3D depicts immunoblots of whole cell and cytosolic extracts of hMSCs.

FIGS. 4A and 4B, is a series of images depicting cell cycle analysis of vehicle, BIO-, and GW-treated cells after 8 days in culture. FIG. 4A is an image depicting DNA content measured by propidium iodide incorporation, followed by fluorescent activated cell sorting. All cultures had similar cell cycle profiles, with the predominant population in G1, suggesting a degree of contact inhibition. Although cells treated with 800 nM BIO were semiconfluent, the cell cycle status of these hMSCs was similar to the other groups, suggesting cell cycle inhibition that was not related to culture density. Representative cultures of control, BIO-, and GW-treated cells counterstained with eosin are presented with the cell cycle profiles to demonstrate the relative culture densities. FIG. 4B is an image depicting immunoblots of cleaved caspase-3 (Asp175) on whole cell extracts of hMSCs treated with BIO or GW. There is no evidence of caspase 3 processing. Note the potential cross reactivity with procaspase 3. Blots were normalized with GAPDH.

FIGS. 5A through 5D, is a series of images depicting hMSCs incubated in osteogenic media with BIO or GW. After 8 days of culture, ALP activity was measured (FIG. 5A) and normalized to cell number (FIG. 5D). OPG and Dkk-1 was measured from the media by ELISA (FIGS. 5B and 5C). Data are means±SD (n=6), p-values p<0.05*, p<0.01**.

FIGS. 7A and 7B, is a series of images depicting hMSCs incubated in osteogenic media containing BIO or GW for 8 days. The cultures then received dex containing osteogenic media for a further 15 days (FIG. 12A). Cultures were stained for calcium with ARS. For semi-quantification, the stain was re-extracted and measured spectrophotometrically. Both BIO (FIG. 7A) and GW (FIG. 7B) pre-treatment enhanced mineralization.

FIGS. 8A and 8B, is a series of imaged depicting osteoinductive properties of clotted human plasma. Confluent cultures were partially overlaid with clotted plasma. FIG. 8A is an image depicting osteogenic medium containing dex or control medium, and differentiation proceeded for 10-20 days. FIG. 8B is an image demonstrating that after 10 days, cultures were stained with ARS to visualize calcium. When treated for 10 days, only the hMSCs in contact with the plasma mineralized.

FIGS. 9A and 9B, is a series of images depicting cultures incubated in osteogenic media containing dex and BIO or GW (FIG. 12B). After 17 days, monolayers were stained for calcium with ARS (FIG. 9A). For semi-quantification, the stain was re-extracted and measured spectrophotometrically (FIG. 9B).

FIGS. 10A through 10D, is a series of images depicting immunohistochemistry of 24-h-old calvarial lesions loaded with GFP-labeled hMSCS. (10A and 10B) GFP-labeled hMSCs administered above the lesion (arrowed). (10C and 10D) Immunocytochemistry for hMSCs by using an anti-human β-2 microglobulin antibody. The staining is localized exclusively to the GFP-labeled hMSCs, with the expected membranous distribution (10D Inset).

FIGS. 11A and 11B, is a series of images depicting 3 mm diameter calvarial defects induced in nude mice. One million hMSCs pretreated with BIO or GW were mixed with plasma and administered to the bone lesion. Subsequent doses were injected at 14 day intervals until day 50 (FIG. 12C). FIG. 11A depicts x-rays of explanted crania. For the GW group, specimens representing the range of the standard deviations are presented. FIG. 11B depicts the ratio of lesioned to contralateral (intact side) radio-opacity calculated by image analysis software. Data are means±SD (n=6, n=5 for mock) p-values *<0.05, **<0.01.

FIG. 12, comprising FIGS. 12A through 12C, is a series of imaged depicting experimental timelines. FIG. 12A depicts an assay of BIO and GW pretreatment on late-stage osteogenesis. FIG. 12B is an assay simultaneous BIO and GW treatment on late-stage osteogenesis. FIG. 12 C is an assay of in vivo bone repair.

FIGS. 13A through 13D, is a series of images depicting new bone formation in the GW treated groups. FIG. 13A is an image depicting a hematoxylin and eosin (H&E) stained longitudinal sections at the diameter of the lesions. New bone can be observed in the GW treated injuries. FIG. 13B is an image depicting an ultraviolet microscopy of transverse sections for tetracycline (new bone) deposition (arrowed). FIGS. 13C and 13D is a series of images depicting immuno-histochemical staining of hMSCs embedded in new bone of the GW treated calvaria. Unstained murine osteoblasts (mOB) are also visible.

FIGS. 14A and 14B, is a series of images demonstrating that GW treatment did not affect the ability of MSCs to initiate angiogenesis at trauma sites. FIG. 14A is an image demonstrating that blood vessels were identified on hematoxylin/eosin-stained sections (arrowed) corresponding to 0.5 mm either side of the diameter of the lesion. FIG. 14B is an image depicting six μm sections that were surveyed every 30 μm and blood vessel area was calculated. Data are means±SD (n=3 animals).

FIGS. 16A through 16D, is a series of images of Extracellular Matrix (ECM) that was extracted from MSC's after three or six weeks of osteogenic differentiation following the protocol shown in FIG. 15. Short-term culture produces malleable constructs (FIGS. 16A, 16B), whereas increased calcification after long-term culture creates more brittle material (FIG. 16C, 16D). Trypsin-treated ECM (FIGS. 161A, 16C) is more fibrous than untreated ECM (FIG. 16B, 16D). Bar=1 mm.

FIGS. 18A through 18H, is a series of images depicting fluorescence microscopy of constructs seeded with GFP-positive MSC's showing even population of the surface of untreated (FIGS. 18A-18C) and trypsin-treated matrices (FIGS. 18D-18F, 40×). Electron microscopy showed the presence of regular fibrils in untreated (FIG. 18G) and treated matrices (FIG. 18H, original magnification: 5000×).

FIG. 19A through FIG. 19F, is a series of images depicting fluorescence imaging confirming presence of GFP-positive MSC's after 17 days of co-culture on untreated (FIG. 19A) or trypsin-treated matrices (FIG. 19D). Alkaline phosphatase (ALP) staining of constructs revealed ALP activity on the matrices (FIG. 19B and FIG. 19E) when compared to non-stained controls (FIG. 19C and FIG. 19F). Note the higher density of the trypsin-treated samples (FIG. 19D-FIG. 19F) when compared to the untreated samples (FIG. 19A-FIG. 19C, original magnification: 100×).

FIG. 20, is a chart depicting the influence of the Wnt modulator 7AIPM on osteogenic differentiation was examined by treating monolayers of MSC's with osteogenic medium containing increasing doses of the compound or vehicle. After four days, alkaline phosphatase (ALP) activity and cell numbers were measured. A typical biphasic dose dependant effect was observed.

FIG. 21, comprising FIGS. 21A and 21B, is a series of images depicting the gene ontology categorization of up-regulated genes in GW9662- and BIO-treated hMSCs.

FIG. 22 is a chart summarizing the differential expression of collagens and extracellular matrix components in hMSCs following treatment with GW9662 or BIO.

FIG. 23 is a chart depicting gene ontology categorization of down-regulated genes in GW9662- and BIO-treated hMSCs.

FIG. 24 is a chart depicting gene ontology categorization of up-regulated genes in BIO-treated hMSCs.

FIG. 25 is a chart depicting inflammatory cytokine expression in hMSCs treated with GW9662 or BIO.

FIG. 26 is a chart depicting confirmation of GW9662 microarray data by ELISA.

FIG. 27 is a chart depicting cell counts from lesioned calvaria after 50 days of treatment.

DETAILED DESCRIPTION

Figure 1:
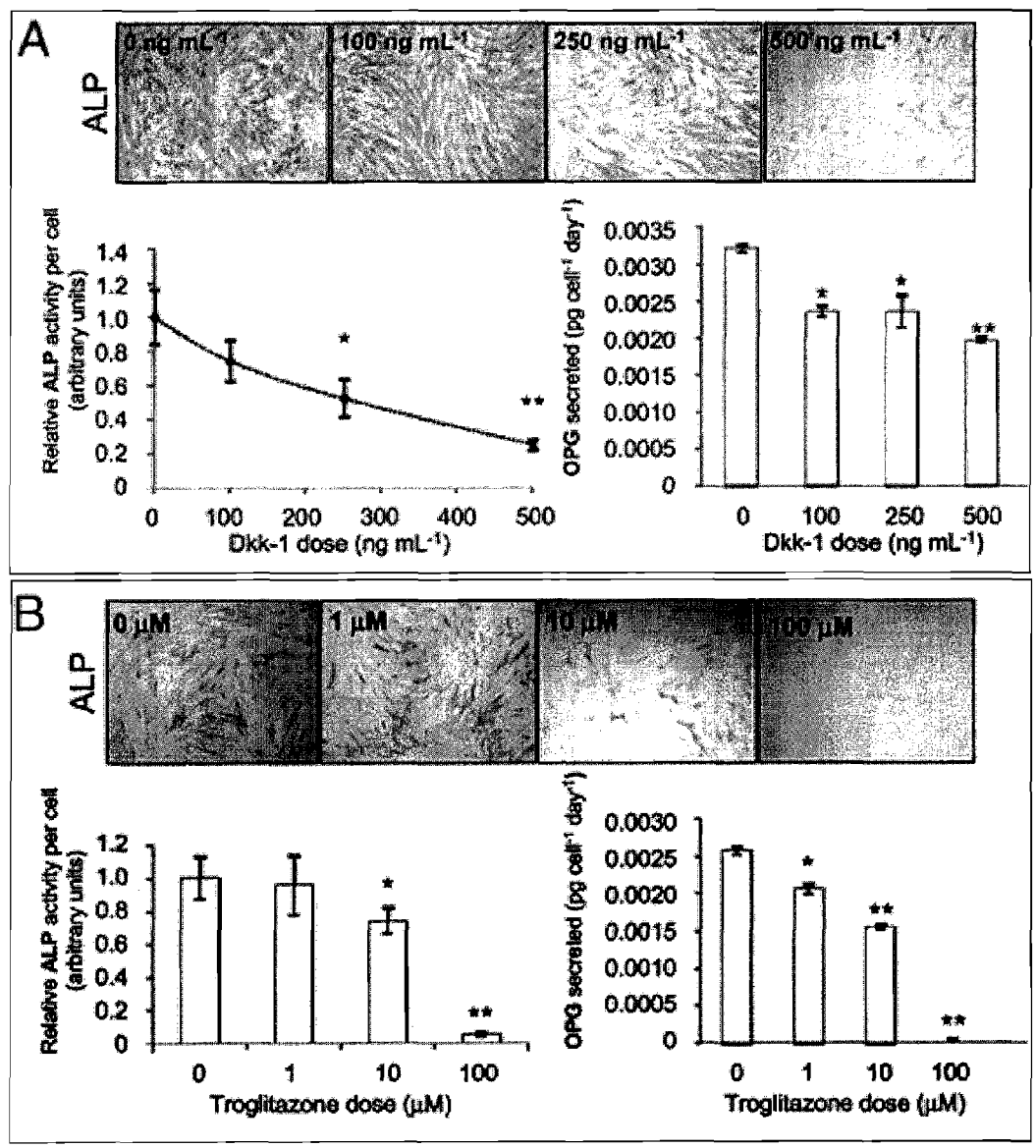
FIG. 1, comprising

The present invention relates to the discovery that mesenchymal stem cells (MSCs) can be manipulated in culture to possess desirable characteristics and therefore can be useful in therapy of a desired disease. For example, the MSCs can be used to treat diseases or disorder of the bone. This is because the MSCs of the invention can be manipulated to possess desirable osteogenic characteristics.

In one embodiment, the invention provides an osteogenic composition comprising MSCs pre-cultured in the presence of an agent that accelerates canonical Wnt signaling therein. In some instances, the osteogenic composition comprises a biocompatible gel to incorporate the MSCs therein. An example of a biocompatible gel is clotted plasma. In some instances, the pre-cultured MSC may be partially differentiated into primitive osteoblasts.

In one embodiment, the agent that accelerates canonical Wnt signaling is an inhibitor of glycogen synthetase kinase-3-beta (GSK3β). An example of a GSK3β inhibitor includes but is not limited to bromo-indirubin-oxime, bromo-indirubin-3'-mono-oxide (BIO), 7-azaindolyl-pyrazinylmaleimide (7AIPM), and the like.

In one embodiment, the agent that accelerates canonical Wnt signaling is an inhibitor of peroxisome proliferator-activated receptor γ (PPARγ). An example of a PPARγ inhibitor is 2-chloro-5-nitro-N-phenyl-benzamide (GW9662).

The present invention provides methods for treating bone degeneration or injury associated with a pathophysiological condition in a mammal by administering to the mammal or contacting the site of injury with the osteogenic composition of the invention.

The invention also provides methods of accelerating repair of a skeletal injury in a mammal by administering to the mammal or contacting the site of injury with the osteogenic composition.

MSCs treated according to the invention can significantly accelerate the repair of bone without the necessity for prosthetic reconstruction, or the requirement for donor bone tissue. The method of the invention therefore has great utility in simplifying the treatment of traumatic bone injury. Furthermore, this method can dramatically accelerate the healing of less severe fractures, allowing recipients to regain mobility after a shorter duration.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

"Alloantigen" is an antigen that differs from an antigen expressed by the recipient.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, the term "biocompatible lattice," is meant to refer to a substrate that can facilitate formation into three-dimensional structures conducive for tissue development. Thus, for example, cells can be cultured or seeded onto such a biocompatible lattice, such as one that includes extracellular matrix material, synthetic polymers, cytokines, growth factors, etc. The lattice can be molded into desired shapes for facilitating the development of tissue types. Also, at least at an early stage during culturing of the cells, the medium and/or substrate is supplemented with factors (e.g., growth factors, cytokines, extracellular matrix material, etc.) that facilitate the development of appropriate tissue types and structures.

"Bioactive agents," as used herein, can include one or more of the following: chemotactic agents; therapeutic agents (e.g., antibiotics, steroidal and non-steroidal analgesics and anti-inflammatories (including certain amino acids such as glycine), anti-rejection agents such as immunosuppressants and anti-cancer drugs); various proteins (e.g., short term peptides, bone morphogenic proteins, collagen, hyaluronic acid, glycoproteins, and lipoprotein); cell attachment mediators; biologically active ligands; integrin binding sequence; ligands; various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin derived growth factor (e.g., IGF-1, IGF-II) and transforming growth factors (e.g., TGFβ I-III), parathyroid hormone, parathyroid hormone related peptide, bone morphogenic proteins (e.g., BMP-2, BMP-4; BMP-6; BMP-7; BMP-12; BMP-13; BMP-14), sonic hedgehog, growth differentiation factors (e.g., GDF5, GDF6, GDF8), recombinant human growth factors (e.g., MP52, and MP-52 variant rhGDF-5), cartilage-derived morphogenic proteins (CDMP-1; CDMP-2, CDMP-3)); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate. Suitable effectors likewise include the agonists and antagonists of the agents described above. The growth factor can also include combinations of the growth factors described above. In addition, the growth factor can be autologous growth factor that is supplied by platelets in the blood. In this case, the growth factor from platelets will be an undefined cocktail of various growth factors. If other such substances have therapeutic value in the orthopedic field, it is anticipated that at least some of these substances will have use in the present invention, and such substances should be included in the meaning of "bioactive agent" and "bioactive agents" unless expressly limited otherwise. Preferred examples of bioactive agents include culture media, bone morphogenic proteins, growth factors, growth differentiation factors, recombinant human growth factors, cartilage-derived morphogenic proteins, hydrogels, polymers, antibiotics, anti-inflammatory medications, immunosuppressive mediations, autologous, allogenic or xenologous cells such as stem cells, chondrocytes, fibroblast and proteins such as collagen and hyaluronic acid. Bioactive agents can be autologus, allogenic, xenogenic or recombinant.

The term "biologically compatible carrier" or "biologically compatible medium" refers to reagents, cells, compounds, materials, compositions, and/or dosage formulations which are suitable for use in contact with the tissues of human beings and animals without excessive toxicity, irritation, allergic response, or other complication commensurate with a reasonable benefit/risk ratio.

As used herein, the term "bone condition (or injury or disease)" refers to disorders or diseases of the bone including, but not limited to, acute, chronic, metabolic and non-metabolic conditions of the bone. The term encompasses conditions caused by disease, trauma or failure of the tissue to develop normally. Examples of bone conditions include, but are not limited, a bone fracture, a bone/spinal deformation, osteosarcoma, myeloma, bone dysplasia, scoliosis, osteoporosis, osteomalacia, rickets, fibrous osteitis, renal bone dystrophy, and Paget's disease of bone.

As used herein, the term "bone marrow stromal cells," "stromal cells," "mesenchymal stem cells," "mesenchymal stromal cells" or "MSCs" are used interchangeably and refer to a cell derived from bone marrow (reviewed in Prockop, 1997), peripheral blood (Kuznetsov et al., 2001), adipose tissue (Guilak et al., 2004), umbilical cord blood (Rosada et al., 2003), synovial membranes (De Bari et al., 2001), and periodontal ligament (Seo et al., 2005). MSCs are characterized by their ability to adhere to plastic tissue culture surfaces (Friedenstein et al.; reviewed in Owen & Friedenstein, 1988), and by being an effective feeder layers for hematopoietic stem cells (Eaves et al., 2001). In addition, MSCs can be differentiated both in culture and in vivo into osteoblasts and chondrocytes, into adipocytes, muscle cells (Wakitani et al., 1995) and cardiomyocytes (Fukuda and Yuasa, 2006), into neural precursors (Woodbury et al., 2000; Deng et al., 2001, Kim et al., 2006; Mareschi et al., 2006; Krampera et al., 2007). Mesenchymal stem cells (MSCs) may be purified using methods known in the art (Wakitani et al., 1995; Fukuda and Yuasa, 2006; Woodbury et al., 2000; Deng et al., 2001; Kim et al., 2006; Mareschi et al., 2006; Krampera et al., 2007).

"Differentiation medium" is used herein to refer to a cell growth medium comprising an additive or a lack of an additive such that a stem cell, adipose derived adult stromal cell or other such progenitor cell, that is not fully differentiated when incubated in the medium, develops into a cell with some or all of the characteristics of a differentiated cell.

As used herein "endogenous" refers to any material from or produced inside an organism, cell or system.

"Exogenous" refers to any material introduced from or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

By "growth factors" is intended the following non-limiting factors including, but not limited to, growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor (EGF), fibroblast growth factor (FGF), nerve growth factor, ciliary neurotrophic factor, platelet derived growth factor (PDGF), and bone morphogenetic protein at concentrations of between picogram/ml to milligram/ml levels.

As used herein, the term "growth medium" is meant to refer to a culture medium that promotes growth of cells. A growth medium will generally contain animal serum. In some instances, the growth medium may not contain animal serum.

An "isolated cell" refers to a cell which has been separated from other components and/or cells which naturally accompany the isolated cell in a tissue or mammal.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

As used herein, the term "multipotential" or "multipotentiality" is meant to refer to the capability of a stem cell of the central nervous system to differentiate into more than one type of cell.

As used herein, the term "modulate" is meant to refer to any change in biological state, i.e. increasing, decreasing, and the like.

The terms "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. Unlike pluripotent stem cells, lineage-committed progenitor cells are generally considered to be incapable of giving rise to numerous cell types that phenotypically differ from each other. Instead, progenitor cells give rise to one or possibly two lineage-committed cell types.

As used herein, "scaffold" refers to a structure, comprising a biocompatible material, that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

The term "stromal cell medium" as used herein, refers to a medium useful for culturing ADAS cells. An example of a stromal cell medium is a medium comprising DMEM/F 12 Ham's, 10% fetal bovine serum, 100 U penicillin/100 μg streptomycin/0.25 μg Fungizone. Typically, the stromal cell medium comprises a base medium, serum and an antibiotic/antimycotic. However, ADAS cells can be cultured with stromal cell medium without an antibiotic/antimycotic and supplemented with at least one growth factor. Preferably the growth factor is human epidermal growth factor (hEGF). The preferred concentration of hEGF is about 1-50 ng/ml, more preferably the concentration is about 5 ng/ml. The preferred base medium is DMEM/F12 (1:1). The preferred serum is fetal bovine serum (FBS) but other sera may be used including horse serum or human serum. Preferably up to 20% FBS will be added to the above media in order to support the growth of stromal cells. However, a defined medium could be used if the necessary growth factors, cytokines, and hormones in FBS for stromal cell growth are identified and provided at appropriate concentrations in the growth medium. It is further recognized that additional components may be added to the culture medium. Such components include but are not limited to antibiotics, antimycotics, albumin, growth factors, amino acids, and other components known to the art for the culture of cells. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 μg/ml. However, the invention should in no way be construed to be limited to any one medium for culturing stromal cells. Rather, any media capable of supporting stromal cells in tissue culture may be used.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. Preferably, the transplant is a human neural stem cell.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Wnt proteins form a family of highly conserved secreted signaling molecules that regulate cell-to-cell interactions during embryogenesis. The terms "Wnts" or "Wnt gene product" or "Wnt polypeptide" when used herein encompass native sequence Wnt polypeptides, Wnt polypeptide variants, Wnt polypeptide fragments and chimeric Wnt polypeptides.

The term "agonist" refers to an agent or analog that binds productively to a receptor and mimics its biological activity. The term "antagonist" refers to an agent that binds to receptors but does not provoke the normal biological response. Thus, an antagonist potentiates or recapitulates, for example, the bioactivity of patched, such as to repress transcription of target genes. The term "Wnt antagonist" as used herein refers not only to any agent that may act by directly inhibiting the normal function of the Wnt protein, but also to any agent that inhibits the Wnt signaling pathway, and thus recapitulates the function of Wnt. The term "Wnt agonist" likewise refers to an agent which antagonizes or blocks the bioactivity of Wnt, such as to increase transcription of target genes.

Description

The present invention provides methods for treating MSCs with an agent that enhances Wnt signaling in the MSC so that the treated MSC exhibits an enhanced osteogenic characteristic compared to an otherwise identical MSC not treated with the agent. The treated MSC produced by the methods of the invention are useful in providing a source of cells for research or transplantation. Thus, in one aspect, the invention provides a method of treating MSCs to enhance the capacity of the MSCs for osteogenic cytotherapy comprising contacting the cells with an agent that enhances Wnt signaling in the cell.

The present invention relates to the discovery that contacting an MSC with an agent that enhances Wnt signaling in the cell enhances the osteogenic characteristic of the MSC. Preferably, the MSC is human MSC. In some instances, the agent can be contacted with any desirable cell having the ability to differentiate into a bone cell to increase the osteogenic characteristic of the cell.

The cells of the invention are useful for treating a bone degeneration or bone injury in a mammal. In some instances, the bone degeneration or injury may be associated with a cancer. The cancer may be a solid cancer, for example osteosarcoma, or a disseminated cancer, e.g., multiple myeloma, or a cancer that metastasizes to the bone, such as, breast cancer or prostate cancer. Also, the bone degeneration or injury may be associated with or may result from osteoporosis, osteogenesis imperfecta, or severe cranial injury. In addition, the bone injury may result from a fracture or a break from trauma resulting from osteoporosis, osteogenesis imperfecta or cranial injury or may result from another trauma.

Pre-Treatment

The invention comprises the treatment of a cell having the potential to differentiate into a bone cell to enhance the osteogenic characteristic of the cell. Preferably, the cell having the differentiation potential is an MSC. While the invention is not bound by any theory of operation, it is believed that treatment of the MSC with an agent that enhances Wnt signaling in the cell enhances the osteogenic characteristic of the cell.

Accordingly, the present invention provides osteogenic compositions or formulations of mesenchymal stem cells (MSC) that are conditioned into becoming predominantly osteogenic upon administration in humans or animals. In one embodiment, the MSCs are pre-cultured in the presence of an agent that enhances Wnt signaling in the cell. In another embodiment, the agent that enhances Wnt signaling in a cell is an inhibitor of, for example, glycogen synthetase kinase-3-beta (GSK3fβ), peroxisome proliferator-activated receptor γ (PPARγ), or a combination thereof. An example of a GSK3p inhibitor includes but is not limited to bromoindirubin-oxime, bromo-indirubin-3'-mono-oxide (BIO), 7-azaindolyl-pyrazinylmaleimide (7AIPM), and the like. An example of a PPARγ inhibitor is 2-chloro-5-nitro-N-phenylbenzamide (GW9662).

In some instances, the MSC is contacted with an agent that enhances Wnt signaling in the cell in a culturing medium. The culturing medium generally comprises a base media. Non-limiting examples of base media useful in the methods of the invention include Minimum Essential Medium Eagle, ADC-1, LPM (Bovine Serum Albumin-free), F10(HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the present invention is DMEM. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62-72, edited by William B. Jakoby and Ira H. Pastan, published by Academic Press, Inc.

Additional non-limiting examples of media useful in the methods of the invention can contain fetal serum of bovine or other species at a concentration of at least 1% to about 30%, preferably at least about 5% to 15%, mostly preferably about 10%. Embryonic extract of chicken or other species can be present at a concentration of about 1% to 30%, preferably at least about 5% to 15%, most preferably about 10%.

In another embodiment, the invention provides a method for differentiating an MSC that has been pre-treated with an agent that enhances Wnt signaling in the cell to express at least one characteristic of a cell of the bone lineage. In some instances, the MCSs are plated to a useful density, including but not limited to a density of about 1,000 to about 500,000 cells/cm$^2$; incubating the cells in a chemically defined culture medium. In one aspect, the MSCs are differentiated to express at least one protein characteristic of a bone cell. In another aspect, the MSCs are differentiated to exhibit a morphological characteristic of a bone derived cell.

Differentiation media useful in the methods of the invention may contain one or more compounds of interest, including, but not limited to, antibiotics, compounds that are osteoinductive, osteoconductive, or promote growth or differentiation, such as bone morphogenetic proteins or other growth factors. Examples of bone morphogenetic proteins include, but are not limited to, osteogenic protein-1, BMP-5, osteogenin, osteoinductive factor and bone morphogenetic protein-4 (Asahina et al. (1996) Exp Cell Res 222:38-47; Takuwa (1991) Biochem Biophys Res Com 174:96-101; Chen (1991) J Bone Min Res 6:1387-1390; Sampath (1992) J Biol Chem 267:20352-20362; Wozney et al. 1988 Science 242:1528-1534, the contents of which are incorporated herein by reference), and the like.

The presence of the differentiated cells of the invention may be detected by a variety of techniques including, but not limited to, flow cytometric, immunohistochemical, in situ hybridization, and/or other histologic or cellular biologic techniques. See, for example, Kopen et al., 1999, Proc Natl Acad Sci 96:10711-10716.

Cells exhibiting at least one characteristic of a bone cell of the invention may be introduced into the bone of a human or animal subject at the site of surgery or fracture. Introduction of an osteogenic cell of the invention to bone is useful in the treatment of bone fractures and bone disorders, including osteoporosis. Thus, in another aspect, the invention is directed to a method of improving a mammal's bone structure, comprising: a) culturing MSCs in a composition which comprises a medium capable of supporting the growth of MSCs and differentiation inducing amounts a differentiation agent in combination with an agent that enhances Wnt signaling in a cell; b) introducing the treated MSC into a surgery or fracture site of a mammal in need thereof mammal.

Preferably, the MSCs are isolated from the mammal into which the treated MSC are to be introduced. However, the MSCs may also be isolated from an organism of the same or different species as the mammal. The mammal may be any organism having bone tissue. Preferably the mammal is a human.

Genetic Modification

The cells of the invention may be stably or transiently transformed with a nucleic acid of interest prior to introduction into a surgery or fracture site of the mammal. Nucleic acid sequences of interest include, but are not limited to those encoding gene products that enhance the growth, differentiation and/or mineralization of bone cells. For example, an expression system for bone morphogenetic protein 4, can be introduced into the MSCs in a stable or transient fashion for the purpose of treating non-healing fractures or osteoporosis. Methods of transformation of MSCs are known to those skilled in the art, as are methods for introducing cells into a bone at the site of surgery or fracture.

In cases in which a gene construct is transfected into a cell, the heterologous gene is operably linked to regulatory sequences required to achieve expression of the gene in the cell. Such regulatory sequences typically include a promoter and a polyadenylation signal.

The gene construct is preferably provided as an expression vector that includes the coding sequence for a heterologous protein operably linked to essential regulatory sequences such that when the vector is transfected into the cell, the coding sequence will be expressed by the cell. The coding sequence is operably linked to the regulatory elements necessary for expression of that sequence in the cells. The nucleotide sequence that encodes the protein may be cDNA, genomic DNA, synthesized DNA or a hybrid thereof, or an RNA molecule such as mRNA.

The gene construct includes the nucleotide sequence encoding the beneficial protein operably linked to the regulatory elements and may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

The regulatory elements for gene expression include: a promoter, an initiation codon, a stop codon, and a polyadenylation signal. It is preferred that these elements be operable in the cells of the present invention. Moreover, it is preferred that these elements be operably linked to the nucleotide sequence that encodes the protein such that the nucleotide sequence can be expressed in the cells and thus the protein can be produced. Initiation codons and stop codons are generally considered to be part of a nucleotide sequence that encodes the protein. However, it is preferred that these elements are functional in the cells. Similarly, promoters and polyadenylation signals used must be functional within the cells of the present invention. Examples of promoters useful to practice the present invention include but are not limited to promoters that are active in many cells such as the cytomegalovirus promoter, SV40 promoters and retroviral promoters. Other examples of promoters useful to practice the present invention include but are not limited to tissue-specific promoters, i.e. promoters that function in some tissues but not in others; also, promoters of genes normally expressed in the cells with or without specific or general enhancer sequences. In some embodiments, promoters are used which constitutively express genes in the cells with or without enhancer sequences. Enhancer sequences are provided in such embodiments when appropriate or desirable.

The cells of the present invention can be transfected using well known techniques readily available to those having ordinary skill in the art. Exogenous genes may be introduced into the cells using standard methods where the cell expresses the protein encoded by the gene. In some embodiments, cells are transfected by calcium phosphate precipitation transfection, DEAE dextran transfection, electroporation, microinjection, liposome-mediated transfer, chemical-mediated transfer, ligand mediated transfer or recombinant viral vector transfer.

In some embodiments, recombinant adenovirus vectors are used to introduce DNA with desired sequences into the cell. In some embodiments, recombinant retrovirus vectors are used to introduce DNA with desired sequences into the cells. In other embodiments, standard $CaPO_4$, DEAE dextran or lipid carrier mediated transfection techniques are employed to incorporate desired DNA into dividing cells. In some embodiments, DNA is introduced directly into cells by microinjection. Similarly, well-known electroporation or particle bombardment techniques can be used to introduce foreign DNA into the cells. A second gene is usually co-transfected or linked to the therapeutic gene. The second gene is frequently a selectable antibiotic-resistance gene. Standard antibiotic resistance selection techniques can be used to identify and select transfected cells. Transfected cells are selected by growing the cells in an antibiotic that will kill cells that do not take up the selectable gene. In most cases where the two genes co-transfected and unlinked, the cells that survive the antibiotic treatment contain and express both genes.

In another embodiment, the cells of the invention can be genetically modified, e.g., to express exogenous genes or to repress the expression of endogenous genes. In accordance with this embodiment, the cell is exposed to a gene transfer vector comprising a nucleic acid including a transgene, such that the nucleic acid is introduced into the cell under conditions appropriate for the transgene to be expressed within the cell. The transgene generally is an expression cassette, including a coding polynucleotide operably linked to a suitable promoter. The coding polynucleotide can encode a protein, or it can encode biologically active RNA, such as antisense RNA or a ribozyme. Thus, the coding polynucleotide can encode a gene conferring, for example, resistance to a toxin, a hormone (such as peptide growth hormones, hormone releasing factor, sex hormones, adrenocorticotrophic hormones, cytokines such as interferons, interleukins, and lymphokines), a cell surface-bound intracellular signaling moiety such as cell-adhesion molecules and hormone receptors, and factors promoting a given lineage of differentiation, or any other transgene with known sequence.

The expression cassette containing the transgene should be incorporated into the genetic vector suitable for delivering the transgene to the cell. Depending on the desired end application, any such vector can be so employed to genetically modify the cells (e.g., plasmids, naked DNA, viruses such as adenovirus, adeno-associated virus, herpesvirus, lentivirus, papillomavirus, retroviruses, etc.). Any method of constructing the desired expression cassette within such vectors can be employed, many of which are well known in the art, such as by direct cloning, homologous recombination, etc. The desired vector will largely determine the method used to introduce the vector into the cells, which are generally known in the art. Suitable techniques include protoplast fusion, calcium-phosphate precipitation, gene gun, electroporation, and infection with viral vectors.

It should be understood that the methods described herein may be carried out in a number of ways and with various modifications and permutations thereof that are well known in the art. It should also be appreciated that any theories set forth as to modes of action or interactions between cell types should not be construed as limiting this invention in any manner, but are presented such that the methods of the invention can be more fully understood.

Scaffold The cells of the invention may be introduced alone or in admixture with a composition useful in the repair of bone wounds and defects. Such compositions include, but are not limited to bone morphogenetic proteins, hydroxyapatite/tricalcium phosphate particles (HA/TCP), gelatin, poly-L-lysine, and collagen.

MSCs can be derived in great quantities from the recipient's bone marrow and, using the novel culture conditions, can be induced to differentiate into an osteoprogenitor cell with great capacity to regenerate bone. Confined in biocompatible gels such as, but not limited to, clotted plasma, the cells build new bone at the site and induce the infiltration of new blood vessels which is a critical requirement for bone growth). The treated MSCs also produce a countless number of secreted growth factors, cytokines and structural proteins, including, but not limited to collagen I and BMP2. Since the new material is real bone, and the cells are from the recipient or a compatible donor, rejection and maintenance is not an issue.

The present invention includes using a scaffold to deliver cells to the desired tissue. The cells can be seeded onto or into a three-dimensional scaffold and administered in vivo in a mammal, where the seeded cells proliferate on the framework and form a replacement tissue in vivo in cooperation with the cells of the mammal.

In some aspects of the invention, the scaffold comprises extracellular matrix, cell lysate (e.g., soluble cell fractions), or combinations thereof, of the desired cells. In some embodiments, the scaffold comprises an extracellular matrix protein secreted by the cells of the invention. Alternatively, the extracellular matrix is an exogenous material selected from the group consisting of calcium alginate, agarose, fibrin, collagen, laminin, fibronectin, glycosaminoglycan, hyaluronic acid, heparin sulfate, chondroitin sulfate A, dermatan sulfate, and bone matrix gelatin. In some aspects, the matrix comprises natural or synthetic polymers.

The invention includes biocompatible scaffolds, lattices, self-assembling structures and the like, whether biodegradable or not, liquid or solid. Such scaffolds are known in the art of cell-based therapy, surgical repair, tissue engineering, and wound healing. Preferably the scaffolds are pretreated (e.g., seeded, inoculated, contacted with) with the cells, extracellular matrix, conditioned medium, cell lysate, or combination thereof. In some aspects of the invention, the cells adhere to the scaffold. The seeded scaffold can be introduced into the mammal in any way known in the art, including but not limited to implantation, injection, surgical attachment, transplantation with other tissue, injection, and the like. The scaffold of the invention may be configured to the shape and/or size of a tissue or organ in vivo. For example, but not by way of limitation, the scaffold may be designed such that the scaffold structure supports the seeded cells without subsequent degradation; supports the cells from the time of seeding until the tissue transplant is remodeled by the host tissue; and allows the seeded cells to attach, proliferate, and develop into a tissue structure having sufficient mechanical integrity to support itself.

Scaffolds of the invention can be administered in combination with any one or more growth factors, cells, drugs or other and/or components described elsewhere herein that stimulate tissue formation or otherwise enhance or improve the practice of the invention. The cells to be seeded onto the scaffolds may be genetically engineered to express growth factors or drugs.

In another preferred embodiment, the cells of the invention are seeded onto a scaffold where the material exhibits specified physical properties of porosity and biomechanical strength to mimic the features of natural bone, thereby promoting stability of the final structure and access and egress of metabolites and cellular nutrients. That is, the material should provide structural support and can form a scaffolding into which host vascularization and cell migration can occur. In this embodiment, the desired cells are first mixed with a carrier material before application to a scaffold. Suitable carriers include, but are not limited to, calcium alginate, agarose, types I, II, IV or other collagen isoform, fibrin, poly-lactic/poly-glycolic acid, hyaluronate derivatives, gelatin, laminin, fibronectin, starch, polysaccharides, saccharides, proteoglycans, synthetic polymers, calcium phosphate, and ceramics (i.e., hydroxyapatite, tricalcium phosphate).

The external surfaces of the three-dimensional framework may be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, and agarose.

In some embodiments, it is important to re-create in culture the cellular microenvironment found in vivo. In addition, growth factors, osteogenic inducing agents, and angiogenic factors may be added to the culture medium prior to, during, or subsequent to inoculation of the cells to trigger differentiation and tissue formation by the cells following administration into the mammal.

Therapy

The present invention discloses that the induction of canonical Wnt signaling in an MSC to enhance the osteogenic characteristic of the cell. Induction of Wnt signaling can be accomplished by inhibition of GSKβ, inhibition of PPARγ, or a combination thereof. Indication of Wnt signaling accelerates osteogenic differentiation by MSCs in vivo and in vitro and partially differentiates them into primitive osteoblasts. It is contemplated that these drugs increase bone mineral levels in a variety of bone degenerative diseases including osteoporosis, some forms of malignant bone disease, some forms of osteogenesis imperfecta and also in the treatment of serious skeletal injuries.

The present invention provides compositions and methods for enhancing the osteogenic characteristic of MSCs. Accordingly, the MSCs treated using the methods of the invention can significantly accelerate the repair of a bone injury, disease, or disorder. In some instances, the MSCs of the invention can treat a bone injury, disease, or disorder without the necessity for prosthetic reconstruction, or the requirement for donor bone tissue. Thus, the invention has a great utility in simplifying the treatment of bone injury. Furthermore, the methods can dramatically accelerate the healing of less severe fractures, allowing recipients to regain mobility after a shorter duration.

The invention also provides a method of treating bone degeneration or injury associated with a pathophysiological condition in a mammal, comprising administering to the mammal an effective amount of the osteogenic composition of the invention to accelerate bone repair, thereby treating the bone degeneration or injury. In one embodiment, the method comprises readministering the osteogenic composition periodically. Particularly the osteogenic composition may be readministered about every two weeks.

Administration of the osteogenic composition of the invention may comprise injecting or implanting the same into the site of bone degeneration or injury. In one aspect the bone degeneration or injury may be associated with a cancer. Examples of a cancer are an osteosarcoma, multiple myeloma or a breast or prostate cancer metastasizing to the bone. In another aspect the bone degeneration or injury may be associated with osteoporosis, osteogenesis imperfecta, or severe cranial injury. In yet another aspect the bone injury may be a bone fracture or break.

In yet another embodiment of the present invention there is provided a method for accelerating repair of a skeletal injury in a mammal, comprising directly contacting the site of the skeletal injury with an effective amount of the osteogenic composition described herein to accelerate bone repair. In one embodiment, the method comprises recontacting the site of injury with the osteogenic composition periodically. An example of periodic recontact is about every two weeks. In one embodiment, the step of directly contacting the site of injury comprises injecting or implanting the osteogenic composition directly therein. Also, the skeletal injury may be a bone fracture or break. In addition, the skeletal injury may be associated with osteoporosis, osteogenesis imperfecta, or severe cranial injury.

Also, the present invention also provides methods of treating bone degeneration or injury associated with a pathophysiological condition using the osteogenic compositions provided herein. The cells comprising the composition are mixed with plasma and administered into a site of bone wound or site of bone degeneration by injection or surgical implantation. If desired, cells are re-administered about every 14 days by injection. This procedure accelerates angiogenesis and bone healing faster than untreated MSCs.

Based upon the present disclosure, MSCs can be isolated and expanded in culture in vitro to obtain sufficient numbers of cells for use in the methods described herein provided that the MSCs are cultured in a manner that enhances Wnt signaling in the cells thereby enhancing osteogenic characteristic of the cell. For example, MSCs can be isolated from human bone marrow and cultured in complete medium (DMEM low glucose containing 4 mM L-glutamine, 10% FBS, and 1% penicillin/streptomycin) in hanging drops or on non-adherent dishes. However, the invention should in no way be construed to be limited to any one method of isolating and culturing medium. Rather, any method of isolating and culturing medium should be construed to be included in the present invention provided that the MSCs are cultured in a manner that promotes Wnt signaling in the cell thereby enhancing osteogenic characteristic of the cell.

Any medium capable of supporting MSCs in vitro may be used to culture the MSCs. Media formulations that can support the growth of MSCs include, but are not limited to, Dulbecco's Modified Eagle's Medium (DMEM), alpha modified Minimal Essential Medium (αMEM), and Roswell Park Memorial Institute Media 1640 (RPMI Media 1640) and the like. Typically, 0 to 20% fetal bovine serum (FBS) or 1-20% horse serum is added to the above medium in order to support the growth of MSCs. However, a defined medium can also be used if the growth factors, cytokines, and hormones necessary for culturing MSCs are provided at appropriate concentrations in the medium. Media useful in the methods of the invention may contain one or more compounds of interest, including but not limited to antibiotics, mitogenic or differentiation compounds useful for the culturing of MSCs. The cells may be grown at temperatures between 27° C. to 40° C., preferably 31° C. to 37° C., and more preferably in a humidified incubator. The carbon dioxide content may be maintained between 2% to 10% and the oxygen content may be maintained between 1% and 22%. However, the invention should in no way be construed to be limited to any one method of isolating and culturing MSCs. Rather, any method of isolating and culturing MSCs should be construed to be included in the present invention provided that Wnt signaling is enhanced in the cells.

Another embodiment of the present invention encompasses the route of administering MSCs to the recipient of the transplant. MSCs can be administered by a route which is suitable for the placement of the transplant, i.e. a biocompatible lattice or a donor tissue, organ or cell, to be transplanted. MSCs can be administered systemically, i.e., parenterally, by intravenous injection or can be targeted to a particular tissue or organ, such as bone marrow. MSCs can be administered via a subcutaneous implantation of cells or by injection of the cells into connective tissue, for example, muscle.

The cells of the invention may be administered into a host in order in a wide variety of ways. Preferred modes of administration are parenteral, intraperitoneal, intravenous, intradermal, epidural, intraspinal, intrasternal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter. In one embodiment, the agent and carrier are administered in a slow release formulation such as a direct tissue injection or bolus, implant, microparticle, microsphere, nanoparticle or nanosphere.

MSCs can be suspended in an appropriate diluent. Suitable excipients for injection solutions are those that are biologically and physiologically compatible with the MSCs and with the recipient, such as buffered saline solution or other suitable excipients. The composition for administration can be formulated, produced and stored according to standard methods complying with proper sterility and stability.

The dosage of the MSCs varies within wide limits and may be adjusted to the individual requirements in each particular case. The number of cells used depends on the weight and condition of the recipient, the number and/or frequency of administrations, and other variables known to those of skill in the art.

The cells described herein can be used in combination with any known technique of tissue engineering, including but not limited to those technologies described in patents and publications including U.S. Pat. Nos. 5,902,741 and 5,863,531 to Advanced Tissue Sciences, Inc. as well as, but not limited to: U.S. Pat. No. 6,139,574, Vacanti et al. Vascularized Tissue Regeneration Matrices Formed By Solid Free Form Fabrication Techniques; U.S. Pat. No. 5,759,830, Vacanti et al. Three-Dimensional Fibrous Scaffold Containing Attached Cells For Producing Vascularized Tissue In Vivo; U.S. Pat. No. 5,741,685, Vacanti, Parenchymal Cells Packaged In Immunoprotective Tissue For Implantation; U.S. Pat. No. 5,736,372, Vacanti et al. Biodegradable Synthetic Polymeric Fibrous Matrix Containing Chondrocyte For In Vivo Production Of A Cartilaginous Structure; U.S. Pat. No. 5,804,178, Vacanti et al. Implantation Of Cell-Matrix Structure Adjacent Mesentery, Omentum Or Peritoneum Tissue; U.S. Pat. No. 5,770,417, Vacanti et al. Three-Dimensional Fibrous Scaffold Containing Attached Cells For Producing Vascularized Tissue In Vivo; U.S. Pat. No. 5,770,193, Vacanti et al. Preparation of Three-Dimensional Fibrous Scaffold for Attaching Cells to Produce Vascularized Tissue In Vivo; U.S. Pat. No. 5,709,854, Griffith-Cima et al. Tissue Formation By Injecting A Cell-Polymeric Solution That Gels In Vivo; U.S. Pat. No. 5,516,532, Atala et al. Injectable Non-Immunogenic Cartilage And Bone Preparation; U.S. Pat. No. 5,855,610, Vacanti et al. Engineering Of Strong, Pliable Tissues; U.S. Pat. No. 5,041,138, Vacanti et al. Neomorphogenesis Of Cartilage In Vivo From Cell Culture; U.S. Pat. No. 6,027,744, Vacanti et al. Guided Development and Support Of Hydrogel-Cell Compositions; U.S. Pat. No. 6,123,727, Vacanti et al. Tissue Engineered Tendons And Ligament; U.S. Pat. No. 5,536,656, Kemp et al. Preparation Of Tissue Equivalents By Contraction Of A Collagen Gel Layered On A Collagen Gel; U.S. Pat. No. 5,144,016, Skjak-Braek et al. Alginate Gels; U.S. Pat. No. 5,944,754, Vacanti Tissue Re-Surfacing With Hydrogel-Cell Compositions; U.S. Pat. No. 5,723,331, Tubo et al. Methods And Compositions For The Repair Of Articular Cartilage Defects In Mammals; U.S. Pat. No. 6,143,501, Sittinger et al. Artificial Tissues, Methods For The Production And The Use Thereof; all of which are incorporated herein by reference.

Transplantation

The invention provides an osteogenic composition comprising MSCs pre-cultured in the presence of an agent that accelerates canonical Wnt signaling therein. In using the osteogenic compositions of the invention, one of ordinary skill in this art is well able to formulate the composition with a suitable pharmaceutical carrier, if necessary, for injection or implantation and to determine whether injection or implantation is the most effective means of introducing the osteogenic composition to the site of bone degeneration or injury. Also, one of ordinary skill in the art is well able to determine a sufficient dosage of the osteogenic composition to inject or implant into a mammal. Dosage would be based on at least the location, extent and severity of bone degeneration or injury and on the pathophysiological condition associated therewith.

The present invention encompasses methods for administering cells of the invention to an animal, including a human, in order to treat a disease where the introduction of new, undamaged cells will provide some form of therapeutic relief.

The skilled artisan will readily understand that MSCs can be transplanted into a recipient whereby upon receiving signals and cues from the surrounding milieu, the cells can further differentiate into mature cells in vivo dictated by the neighboring cellular milieu. Alternatively, the MSCs can be differentiated in vitro into a desired cell type and the differentiated cell can be administered to an animal in need thereof.

The invention also encompasses grafting MSCs in combination with other therapeutic procedures to treat disease or trauma in the body. Thus, MSCs can be co-grafted with other cells, both genetically modified and non-genetically modified cells which exert beneficial effects on the patient. Therefore the methods disclosed herein can be combined with other therapeutic procedures as would be understood by one skilled in the art once armed with the teachings provided herein.

The MSCs of this invention can be transplanted into a patient using techniques known in the art such as i.e., those described in U.S. Pat. Nos. 5,082,670 and 5,618,531, each incorporated herein by reference, or into any other suitable site in the body.

Transplantation of the cells of the present invention can be accomplished using techniques well known in the art as well as those described herein or as developed in the future. The present invention comprises a method for transplanting, grafting, infusing, or otherwise introducing the cells into a mammal, preferably, a human. Exemplified herein are methods for transplanting the cells into bone tissue of various mammals, but the present invention is not limited to such anatomical sites or to those mammals. Also, methods that relate to bone transplants are well known in the art and are described for example, in U.S. Pat. No. 4,678,470 and U.S. Pat. No. 5,571,083, teaches methods for transplanting cells to any anatomical location in the body.

The cells may also be encapsulated and used to deliver biologically active molecules, according to known encapsulation technologies, including microencapsulation (see, e.g., U.S. Pat. Nos. 4,352,883; 4,353,888; and 5,084,350, herein incorporated by reference), or macroencapsulation (see, e.g., U.S. Pat. Nos. 5,284,761; 5,158,881; 4,976,859; and 4,968,733; and International Publication Nos. WO 92/19195; WO 95/05452, all of which are incorporated herein by reference). For macroencapsulation, cell number in the devices can be varied; preferably, each device contains between $10^3$-$10^9$ cells, most preferably, about $10^5$ to $10^7$ cells. Several macroencapsulation devices may be implanted in the patient. Methods for the macroencapsulation and implantation of cells are well known in the art and are described in, for example, U.S. Pat. No. 6,498,018.

The dosage of the MSCs varies within wide limits and may be adjusted to the individual requirements in each particular case. The number of cells used depends on the weight and condition of the recipient, the number and/or frequency of administration, and other variables known to those of skill in the art.

The number of MSCs administered to a patient may be related to, for example, the cell yield after processing. A portion of the total number of cells may be retained for later use or cyropreserved. In addition, the dose delivered depends on the route of delivery of the cells to the patient. In one embodiment of the invention, a number of cells to be delivered to the patient is expected to be about $5.5 \times 10^4$ cells. However, this number can be adjusted by orders of magnitude to achieve the desired therapeutic effect.

The mode of administration of the cells of the invention to the patient may vary depending on several factors including the type of disease being treated, the age of the mammal, whether the cells are differentiated or not, whether the cells have heterologous DNA introduced therein, and the like. The cells may be introduced to the desired site by direct injection, or by any other means used in the art for the introduction of compounds administered to a patient suffering from a particular disease or disorder.

The MSCs may also be applied with additives to enhance, control, or otherwise direct the intended therapeutic effect. For example, in one embodiment, the cells may be further purified by use of antibody-mediated positive and/or negative cell selection to enrich the cell population to increase efficacy, reduce morbidity, or to facilitate ease of the procedure. Similarly, cells may be applied with a biocompatible matrix which facilitates in vivo tissue engineering by supporting and/or directing the fate of the implanted cells.

Prior to the administration of the MSCs into a patient, the cells may be stably or transiently transfected or transduced with a nucleic acid of interest using a plasmid, viral or alternative vector strategy. The cells may be administered following genetic manipulation such that they express gene products that intended to promote the therapeutic response(s) provided by the cells.

The use of MSCs for the treatment of a disease, disorder, or a condition provides an additional advantage in that the MSCs can be introduced into a recipient without the requirement of an immunosuppressive agent. Successful transplantation of a cell is believed to require the permanent engraftment of the donor cell without inducing a graft rejection immune response generated by the recipient. Typically, in order to prevent a host rejection response, nonspecific immunosuppressive agents such as cyclosporine, methotrexate, steroids and FK506 are used. These agents are administered on a daily basis and if administration is stopped, graft rejection usually results. However, an undesirable consequence in using nonspecific immunosuppressive agents is that they function by suppressing all aspects of the immune response (general immune suppression), thereby greatly increasing a recipient's susceptibility to infection and other diseases.

The present invention provides a method of treating a disease, disorder, or a condition of bone by introducing MSCs or differentiated MSCs of the invention into the recipient without the requirement of immunosuppressive agents. The present invention includes the administration of an allogeneic or a xenogeneic MSCs, or otherwise an MSC that is genetically disparate from the recipient, into a recipient to provide a benefit to the recipient. The present invention provides a method of using MSCs or differentiated MSCs of the invention to treat a disease, disorder or condition without the requirement of using immunosuppressive agents when administering the cells to a recipient. There is therefore a reduced susceptibility for the recipient of the transplanted MSC or differentiated MSC of the invention to incur infection and other diseases, including cancer relating conditions that is associated with immunosuppression therapy.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations which are evident as a result of the teachings provided herein.

The following experiments were performed to investigate the role of Wnt signaling and osteogenesis by human MSCs. An inhibitor of GSK3β that would be predicted to mimic Wnt signaling through direct stabilization of β-catenin (bromo-indirubin-3'-mono-oxime, BIO) and an inhibitor of PPARγ (GW9662, or GW) that would be predicted to attenuate inhibitory crosstalk from the adipogenic axis and therefore also enhance Wnt signaling (Farmer, 2005, Int J Obes (Lond). 29:13-16; Akune et al., 2004, J Clin Invest 113:846-855; Liu et al., 2004, J Biol Chem 279:45020-45027) were compared. It was observed that both BIO and GW increased in vitro mineralization, but expression of early osteogenic markers was biphasic, with higher doses becoming inhibitory. When implanted into mice harboring calvarial defects, hMSCs pre-treated with GW substantially accelerated healing. It was observed that GW treatment significantly reduced expression of chemokines that may exacerbate neutrophil and macrophage mediated cell rejection. These data suggest that use of PPARγ inhibitors during the preparation of hMSCs substantially and reliably enhances the capacity of hMSCs for osteogenic cytotherapy.

Example 1

Pharmaceutical Modulation of Canonical Wnt Signaling in Multipotent Stromal Cells for Improved Osteoinductive Therapy Human mesenchymal stem cells (hMSCs) from bone marrow are regarded as putative osteoblast progenitors in vivo and differentiate into osteoblasts in vitro. Positive signaling by the canonical wingless (Wnt) pathway is critical for the differentiation of MSCs into osteoblasts. In contrast, activation of the peroxisome proliferator-activated receptor-γ (PPARγ) mediated pathway results in adipogenesis. Experiments were designed to compare the effects of glycogen-synthetase-kinase-3β (GSK3β) inhibitors and PPARγ inhibitors on osteogenesis by hMSCs. Both compounds altered the intracellular distribution of β-catenin and GSK3β in a manner consistent with activation of Wnt signaling. With osteogenic supplements, the GSK3β inhibitor bromo-indirubin-3'-monooxime (BIO) and the PPARγ inhibitor GW9662 (GW) enhanced early osteogenic markers, alkaline phosphatase (ALP) and osteoprotegerin (OPG) by hMSCs and transcriptome analysis demonstrated upregulation of genes encoding bone-related structural proteins. At higher doses of the inhibitors, ALP levels were attenuated, but dexamethasone-induced biomineralization was accelerated. When hMSCs were pretreated with BIO or GW and implanted into experimentally induced non-self healing calvarial defects, GW treatment substantially increased the capacity of the cells to repair the bone lesion. Furthermore, it was observed that GW treatment significantly reduced expression of chemokines that may exacerbate neutrophil and macrophage mediated cell rejection. These data suggest that use of PPARγ inhibitors during the preparation of hMSCs may enhance the capacity of the cells for osteogenic cytotherapy.

The materials and methods employed in the experiments disclosed herein are now described.

Tissue Culture

Iliac crest bone marrow aspirates (2 mL) were drawn in accordance with institutional review board approval. Mesenchymal stem cells were prepared from the mononuclear fraction of the aspirates as previously described (Colter et al., 2000, Proc Natl Acad Sci USA 96:7294-7299; Sekiya et al., 2002, Stem Cells 20:530-541).

Human MSCs were cultured in α-MEM (Invitrogen, Carlsbad, Calif.) containing 20% (vol/vol) FBS (Atlanta Biologicals), 100 units·mL-1 penicillin, 1 μg·mL-1 streptomycin, and 4 mM L-glutamine. For expansion, cells were plated at an initial seeding density of 100 cells/cm2 and allowed to divide for six to eight doublings until 40-50% confluent. For repassage and experiments, MSCs were recovered with trypsin/EDTA mixture (Invitrogen).

Early Osteogenic Differentiation and Alkaline Phosphatase Assays

MSCs were plated in 6-well plates at an initial plating density of 100 cells per $cm^2$ and cultured in standard complete media for 6 days until semi-confluence (approximately 5,000 cells per $cm^2$). Osteogenic base media consisting of complete media containing 5 mg $mL^{-1}$ β-GP and 50 μg $mL^{-1}$ ascorbate-2-phosphate (Sigma, Poole, Dorset, UK) and the appropriate inhibitor or vehicle was then used to induce early osteogenic differentiation. Assays were allowed to proceed for 8-10 days with changes of media every 2 days. ALP assays were performed as previously described (Gunn et al., 2005, Stem Cells 24:986-991).

Cell Cycle

Profiles were generated by fluorescence activated cell sorting (Beckman Coulter FC500) and analyzed with MultiCycleAV (Pheonix Flow Systems) software.

Array Analysis

Transcriptome arrays were performed using Affimetrix apparatus and HG-U133 Plus 2.0 chips. Cytokine arrays on conditioned media were performed using a human cytokine array (RayBiotech) and analyzed using a digital imager (Versadoc, Bio Rad, Hercules, Calif.).

ELISAs

ELISA for CXCL6, Dkk-1, GROα, GROβ, and OPG were carried out by using nonbiotinylated polyclonal capture antibodies and biotinylated detection antibodies that were commercially acquired (R&D Systems and PromoKine) on Nunc Immunosorp coated 96-well plates (Fisher Lifesciences). The biotinylated capture antibodies were detected by using horseradish peroxidase-conjugated streptavidin and TMB substrate (Pierce). ELISA for IL-1b were performed by using commercially acquired kits.

Protein Extraction, Gel Electrophoresis and Western Blotting

Nuclear extracts were performed by Triton extraction and differential centrifugation as previously described (Gregory et al., 2003, J Biol Chem 278:28067-28078). Proteins were electrophoresed and blotted onto nitrocellulose using the Novex electrophoresis system (Invitrogen, Carlsbad, Calif.).

Late Stage Osteogenesis and ARS Staining

Mature osteogenic assays were performed in 6 well format as previously described (Gregory et al., 2004, Anal Biochem 329:77-84).

Clotted Plasma Co-Culture

Confluent monolayers of MSCs were generated in wells of a 12 well tissue culture plate. Human plasma was added to each well so as to cover approximately 30% of the surface area. After the plasma had clotted osteogenic assays were then performed using standard media preparations.

Calvarial Lesions

MSCs were cultured in the presence of osteogenic base media containing the appropriate inhibitor or vehicle. After 8 days, they were suspended in human plasma and administered to nude mice that had received a circular lesion in the cranium. Subsequent doses of cells were administered by direct injection in plasma/thromboplastin mix.

X-Ray Imaging and Quantification

Cranial bones were imaged by x-ray under anaesthesia (Faxitron M20). Digital images were be captured on a digital plate and processed on a phosphorimager reader (PMI, Biorad) and processed by volume analysis software (Quantity One, Biorad).

Histochemistry and Immunocytochemistry

For β-catenin localization studies, hMSCs were stained with a cy-3 conjugated anti-β-catenin antibody (clone 15B8, Sigma, St. Louis, Mo.) and nuclei were counterstained with pico-green dye (Invitrogen). Specimens were processed as paraffin blocks and 8 µm longitudinal sections were prepared, deparaffinized and rehydrated, then stained with hematoxylin and eosin (Sigma). For immunocytochemistry, sections were probed with an anti-human β-2-microglobulin antibody. An upright fluorescent microscope (Eclipse H600L, Nikon) fitted with a high performance camera (Retiga 2000R) and image analysis software (NiSElements, Nikon) was employed for imaging.

Tetracycline Tracing of In Vivo Calcium Deposition

The tetracycline was imaged using an upright fluorescent microscope (Eclipse H600L, Nikon) fitted with a high performance camera (Retiga 2000R) and analyzed using NiSElements software (Nikon). Embedding, sectioning and mounting was carried out on non-decalcified material.

Semi-Quantitative Blood Vessel Measurements

Calvaria were fixed, decalcified and sectioned in paraffin and stained with hematoxylin and eosin as described. Using NIS-Elements image analysis software, the surface area of blood vessels in a defined ROI was calculated and totaled. The values were expressed as the mean of total blood vessel area from 3 animals per group.

Calvaria were fixed, decalcified, and sectioned in paraffin and stained with hematoxylin and eosin as described. Two-dimensional regions of interest (ROI) were carefully defined and normalized for all specimens. For this purpose, 6-µm-thick longitudinal serial sections were prepared, and those sections containing tissue up to and including 0.5 mm above and below the diameter of the lesion. These were included in the measurements. A 6-µm section was counted every 30 µm (34 sections) within the entire region of interest, which consisted of the longitudinal thickness of the lesion (the thickness of the bone and adjacent fibrous tissue) by the original width of the lesion in one dimension (3 mm) and 0.5 mm above and below the original diameter of the lesion in the final dimension. Using NIS-Elements image analysis software, the surface area of blood vessels in the 2D ROI was calculated for each section and totaled. The values were expressed as the mean of total blood vessel area from three animals per group.

The results of these experiments are now described.

The Effect of Dkk-1 and PPARγ Agonists on the Expression of ALP

Figure 2:
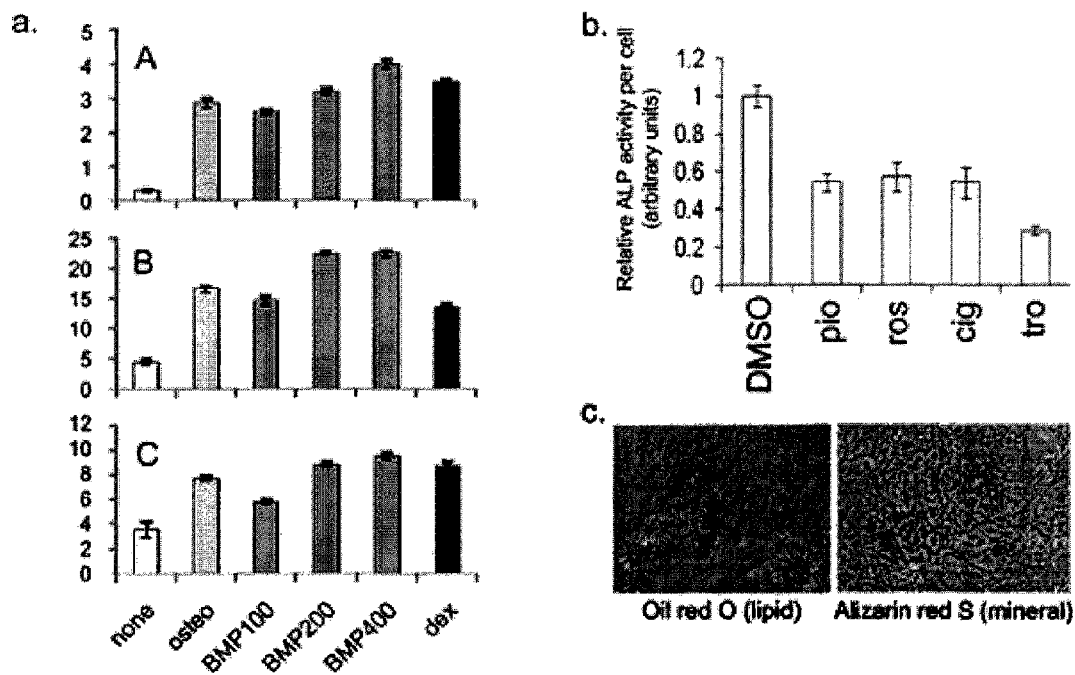
FIG. 2, comprising

To confirm that Wnt signaling is necessary for the differentiation of hMSCs into osteoblasts, MSCs were incubated in osteoinductive media containing no dexamethasone (dex), for 8 days and measured activity of alkaline phosphatase (ALP). Although it is conventional to add dexamethasone for osteogenesis, given its powerful pleiotropic effects and the observation that early osteogenic markers such as ALP can be activated without its presence (FIG. 2A), initial experiments were performed in the absence of dexamethasone. When the Wnt inhibitor Dkk-1 was added to block canonical Wnt signaling, ALP activity was attenuated (FIG. 1A). PPARγ activity was examined on osteogenesis since the PPARγ activity enhances adipogenesis whilst inhibiting the Wnt mediated osteogenic axis of differentiation (Boland et al., 2004, J Cell Biochem 93:1210-30; Farmer, 2005, Int J Obes (Lond). 29:13-16). ALP function was dose-dependently down-regulated upon incubation with troglitazone, and also other synthetic PPARγ agonists (FIG. 1B, FIG. 2).

Figure 3:
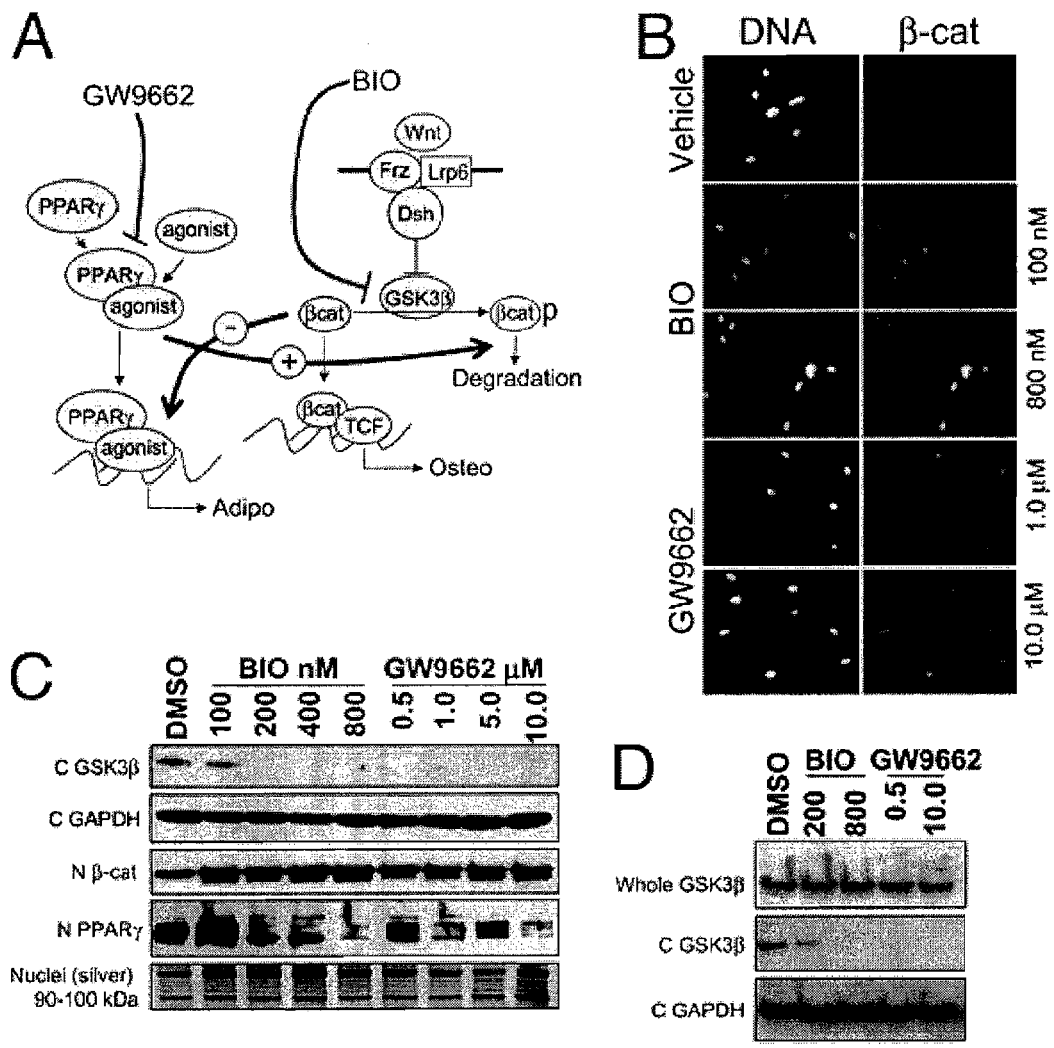
FIG. 3, comprising

The Effect of GSK3β and PPARγ Inhibition on Intracellular Redistribution of GSK3β and β-Catenin The next experiments were designed to examine whether inhibition of GSK3β would mimic Wnt signaling through direct stabilization of β-catenin, and inhibition of PPARγ that would blunt inhibitory crosstalk from the adipogenic axis therefore also resulting in enhancement Wnt signaling (FIG. 3A) (Farmer, 2005, Int J Obes (Lond). 29:13-16; Akune et al., 2004, J Clin Invest 113:846-855; Liu et al., 2004, J Biol Chem 279:45020-45027). The inhibitors BIO and GW were chosen due to their specificity for GSK3β and PPARγ respectively (FIG. 3A). Incubation of both inhibitors with MSCs under osteogenic conditions resulted in increased levels of nuclear β-catenin (FIG. 3B, 3C) and depletion of GSK3β from the cytoplasm (FIG. 3D). Interestingly, cytosolic depletion of GSK3β occurred, even though the proposed mechanism of BIO or GW does not predict up-regulation of a Wnt/Frz/LRP/Dsh receptor complex. Without wishing to be bound by any particular theory, both nuclear localization of β-catenin and depletion of cytosolic GSK3β are consistent with enhancement of canonical Wnt signaling. Furthermore, incubation of hMSCs in either BIO or GW reduced nuclear levels of PPARγ, also suggesting that the canonical Wnt axis was predominating in the treated cells.

Figure 4:
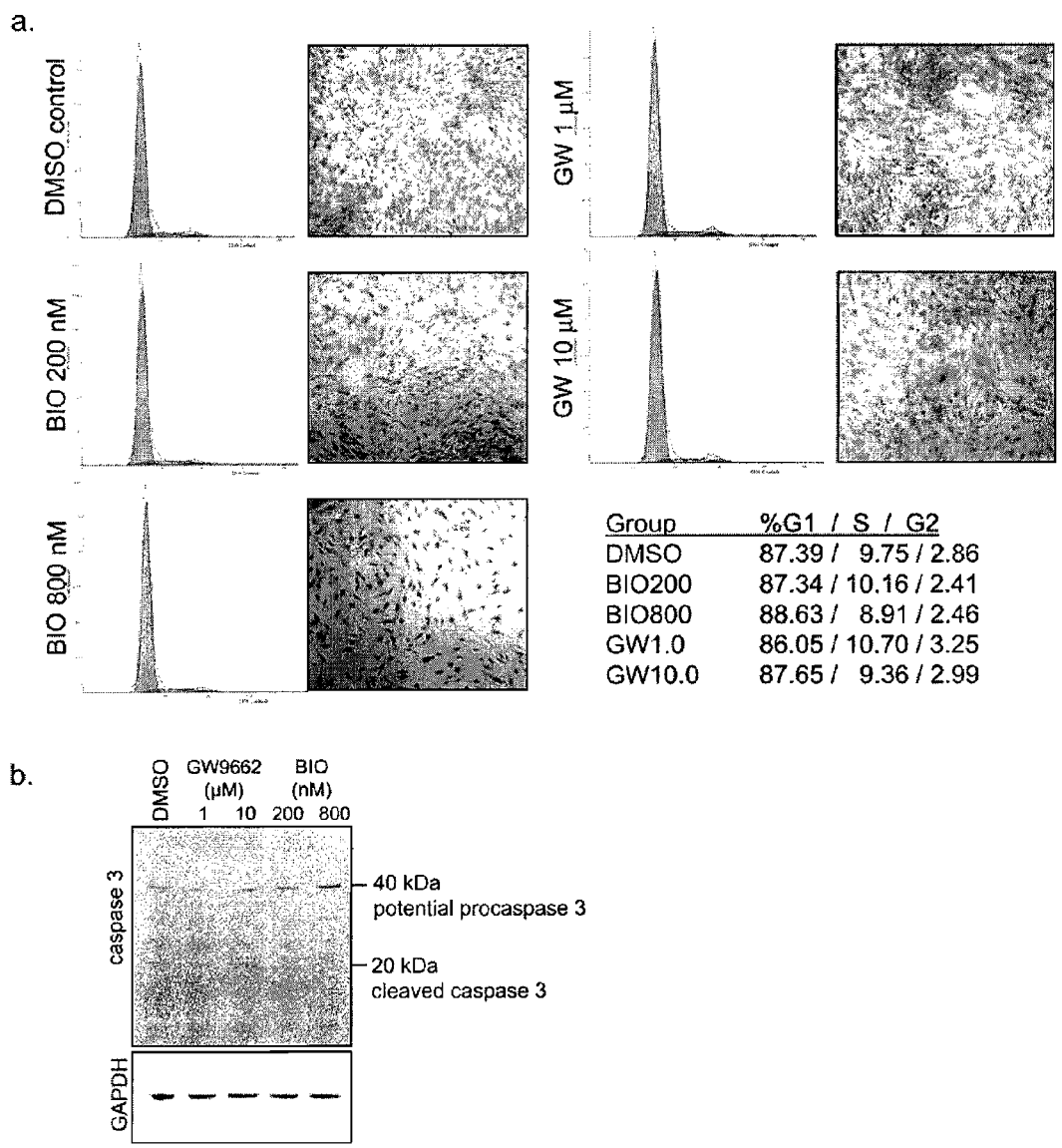
FIG. 4, comprising
Figure 5:
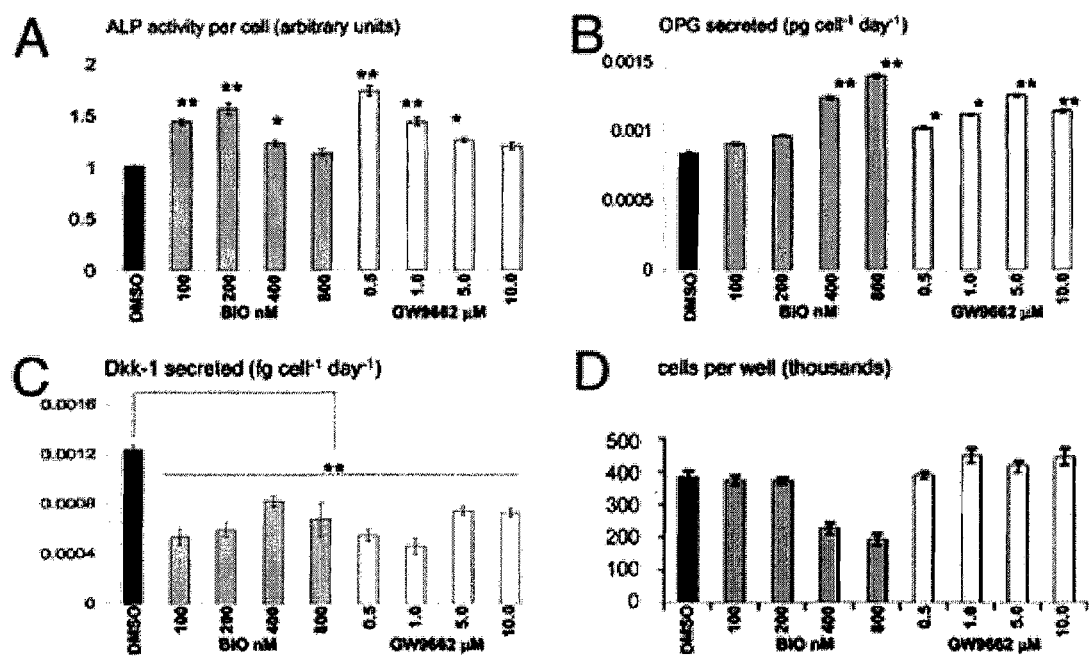
FIG. 5, comprising

The Effect of GSK3β and PPARγ Inhibition on the Expression of ALP, OPG and Dkk-1:

To examine whether the up-regulation of Wnt signaling by the inhibitors affected early stage osteogenesis by MSCs, they were incubated in osteogenic medium lacking dex but containing BIO or GW. After 8 days of culture, ALP activity and the secretion of OPG were measured. Both inhibitors induced the ALP activity, but this was observed at low doses of inhibitor; in the case of BIO, the maximal effect was observed between 100-200 nM and for GW, the effect occurred at doses between 0.5 and 1.0 μM. At higher doses, exceeding 400 nM BIO or 1.0 μM GW, ALP activity dropped back to control levels (FIG. 5A). Secretion of OPG rose in a dose dependent manner upon incubation with BIO, but reached maximal stimulation at 0.5 μM GW (FIG. 5B). It has been speculated that arrest of canonical Wnt signaling occurs during terminal differentiation of osteoprogenitor cells and Dkk-1 has been implicated in this process (van der Horst et al., 2005, J Bone Miner Res 20:1867-1877; Liu et al., 2009, J Cell Biol 185:67-75). Dkk-1 secretion was reduced in all cases, with maximal inhibition occurring at concentrations that induced highest ALP activity (FIG. 5C). Even though Dkk-1 levels were slightly elevated GW and BIO doses, they remained significantly lower than the control. A substantial reduction of hMSC yield was evident when exposed to concentrations greater than 400 nM of BIO. This effect did not seem to arise from canonical Wnt signaling since GW elicited the same effects on β-catenin, GSK3β redistribution and stimulation of early osteogenic markers without reduction in cellular yield. Although BIO is highly specific for GSK3β, (Meijer et al., 2003, Chem Biol 10:1255-1266) the parent molecule; indirubin monooxime has been shown to inhibit cyclin dependent kinases at high concentrations (Damiens et al., 2001, Oncogene 20:3786-3797). Cell cycle analysis demonstrated that hMSCs treated with 800 nM BIO exhibited a similar DNA profile to those that are heavily contact inhibited, suggesting that high doses of BIO inhibit mitosis (FIG. 4A). The absence of apoptotic morphology, a pre-G1 peak (FIG. 4B) and no detectable levels of cleaved caspase 3 confirmed apoptosis was also not responsible for the reduced cell yield.

The Effects of GSK3β and PPARγ Inhibition on the Transcriptome of hMSCs

Inhibition of GSK3β and PPARγ appeared to increase the level of Wnt signaling concomitantly with increased OPG secretion and ALP activity. These observations suggested that the inhibitors had enhanced the early stages of osteogenesis through acceleration of canonical Wnt signaling at the expense of PPARγ activity. To examine this phenomenon in more detail, hMSCs were incubated in osteogenic media lacking dex, but containing high (800 nM BIO and 10 μM GW) and low (200 nM BIO and 1.0 μM GW) doses of the inhibitors. After 8 days of culture, RNA microarrays were performed on the hMSCs. Initial inspection of the datasets demonstrated that they shared similarities with a similar study involving human fibroblasts and Wnt3a suggesting that canonical Wnt signaling had been accelerated. It was observed that Klf-6, caldesmon-1, gamma-aminobutyric acid B receptor-2, synaptotagmin like-2 were significantly up-regulated in Wnt3a treated fibroblasts and both BIO and GW treated hMSCs. Protocadherin-7, PR domain containing-1, gremlin-1, collectin subfamily member-12, stanniocalcin-2 were significantly up-regulated in Wnt3a treated fibroblasts and BIO treated hMSCs only (GW, no change). Fibroblast growth factor-7, high mobility group AT-hook 2, Cdk5 and Abl enzyme substrate-1, amyloid beta precursor protein-binding family B2 were significantly up-regulated in Wnt3a treated fibroblasts GW treated hMSCs only (BIO, no change). Transducin-like enhancer of split-1 were significantly up-regulated in Wnt3a treated fibroblasts but down-regulated in both BIO and GW treated hMSCs.

Figure 6:
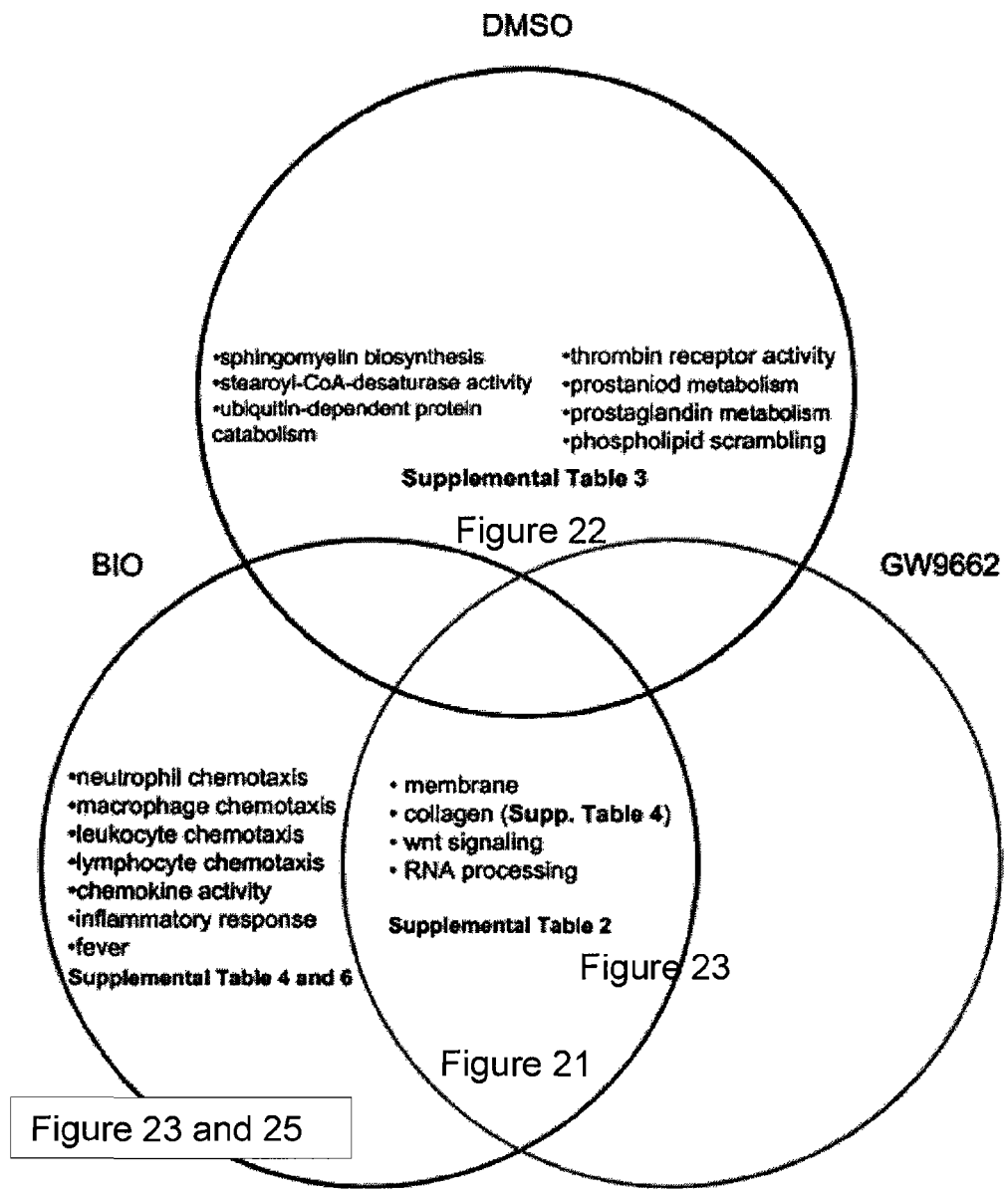
FIG. 6 is a Venn diagram summarizing the major microarray analysis results. Human MSCs were treated with 200 or 800 nM BIO or 1.0 or 10.0 μM GW9662 in osteogenic media for 8 days. RNA was then extracted and subjected to Affimetrix microarray analysis. Results were subjected to hierarchical clustering, and three main clusters were evident—up-regulated in GW9662 and BIO when compared to controls, up-regulated in control cells when compared to BIO and GW9662 groups, and profoundly down-regulated in GW9662 treated cells, but modestly up-regulated in BIO-treated cells when compared to controls. The genes within each cluster were then sorted based on their gene ontology tags (GO tags). The Venn diagram represents the clusters, and the text represents the major GO tag designations within the clusters. Details are presented in supplemental tables. Note that the P values for the clustering were extremely low (in the order of $1 \times 10-6$ to $1 \times 10-100$), demonstrating that the probability of a given set of genes clustering due to random occurrence was virtually zero.

Irrespective of dose, differentially transcribed genes clustered into 2 general groups with strong statistical significance ($p<0.0001$ for all cases, FIG. 6); up-regulated in GW and BIO treated cells compared to the vehicle control (I) and up-regulated in the vehicle control compared to BIO and GW (II). Gene clusters were sorted into gene ontology (GO) tags based on known function. The majority of GO tags in cluster I (FIG. 21) consisted of membrane, mRNA processing, and intracellular rearrangement-related functions as well as collagen and extracellular matrix (ECM) groups. The Wnt/β-catenin GO group was also significantly represented in this cluster. Upon examination of individual fold-changes for differentially expressed ECM genes it was evident that collagens and ECM proteins found in bone tissue were up-regulated whereas those found in other tissues were reduced or unchanged (FIG. 24). Of interest was the down-regulation of matrix metalloproteinase I, matrix gla-protein and oncostatin M, all associated with inhibition of osteogenesis or bone catabolism. Cluster II consisted mainly of genes responsible for steroid and lipid processing (FIG. 23). Of note was the prevalence of prostaglandin and lipid modifying enzymes in this cluster because these processes often provide ligands for PPARγ (Kota et al., 2005, Pharmacol Res 51:85-94) as well as enrichment of sphingomyelin and ceramide related genes, which are strongly associated with lipid and steroid homeostasis (Lucki et al., 2008, Subcell Biochem 49:387-412; Worgall, 2008, Subcell Biochem 49:371-385).

The Effect of GSK3β and PPARγ Inhibition on Late Stage Osteogenesis

Figure 7:
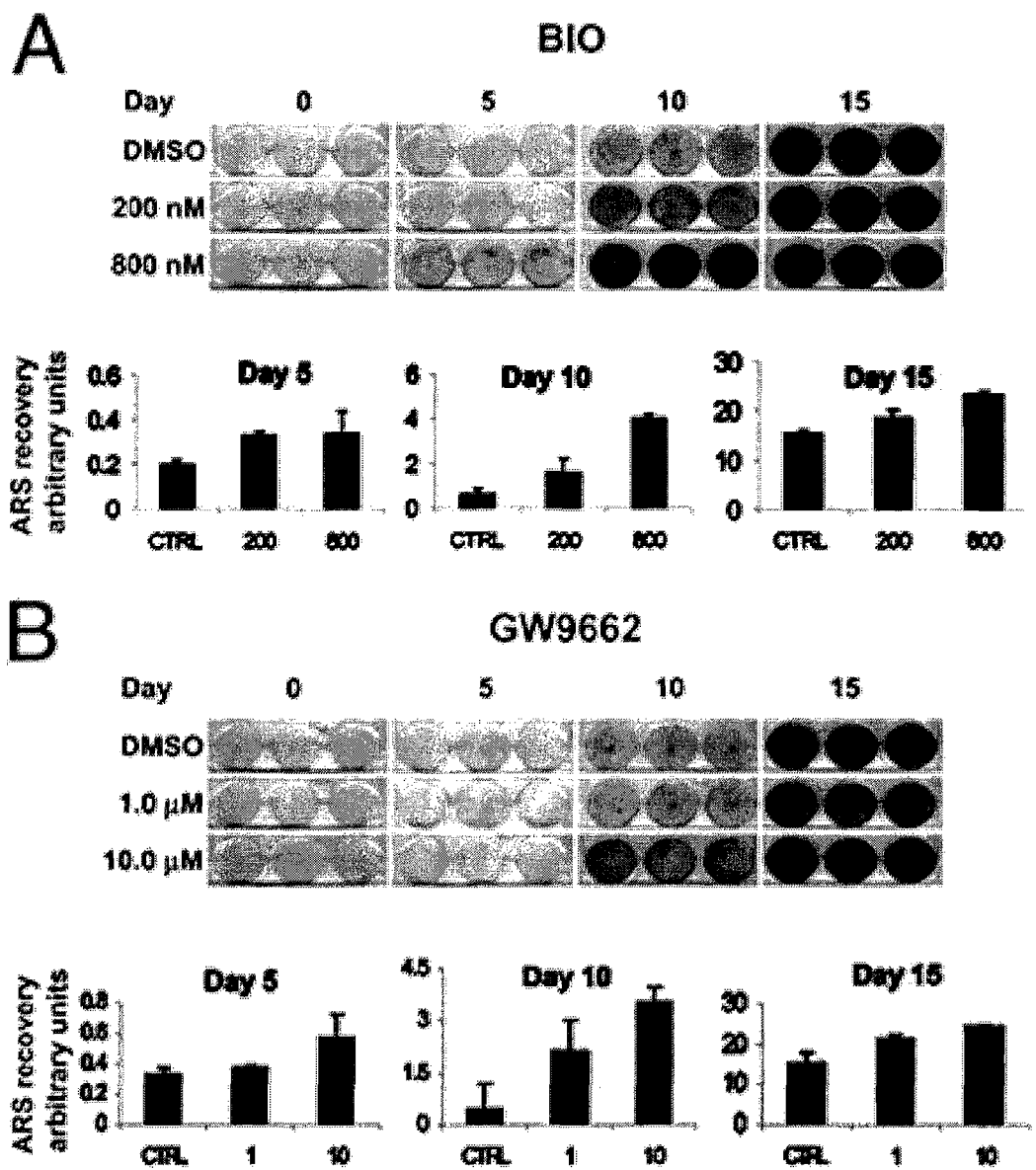
FIG. 7, comprising

Extended periods of incubation in BIO and GW in the absence of dex did not induce biomineralization, so therefore experiments were designed to measure the effect of the inhibitors in its presence. Initially, experiments were conducted to examine whether pre-treatment of hMSCs with inhibitors BIO (200 and 800 nM) and GW (1.0 and 10.0 μM) in the presence of β-glycerophosphate (β-GP) and ascorbate for 8 days followed by 15 days in the same media supplemented with dex affected mineralization of the cultures. If BIO or GW function to accelerate the cells through the immature stages of osteogenesis and partially to maturity, hMSCs exposed to these conditions would be expected to respond more rapidly to the steroid-dependent mature osteoblast transition. After differentiation, calcium content was visualized by Alizarin Red S (ARS) staining and the dye was extracted and quantified. At the doses tested, and in a dose-dependent manner, BIO and GW enhanced dex-induced differentiation into biomineralizing osteoblasts (FIG. 7).

Figure 9:
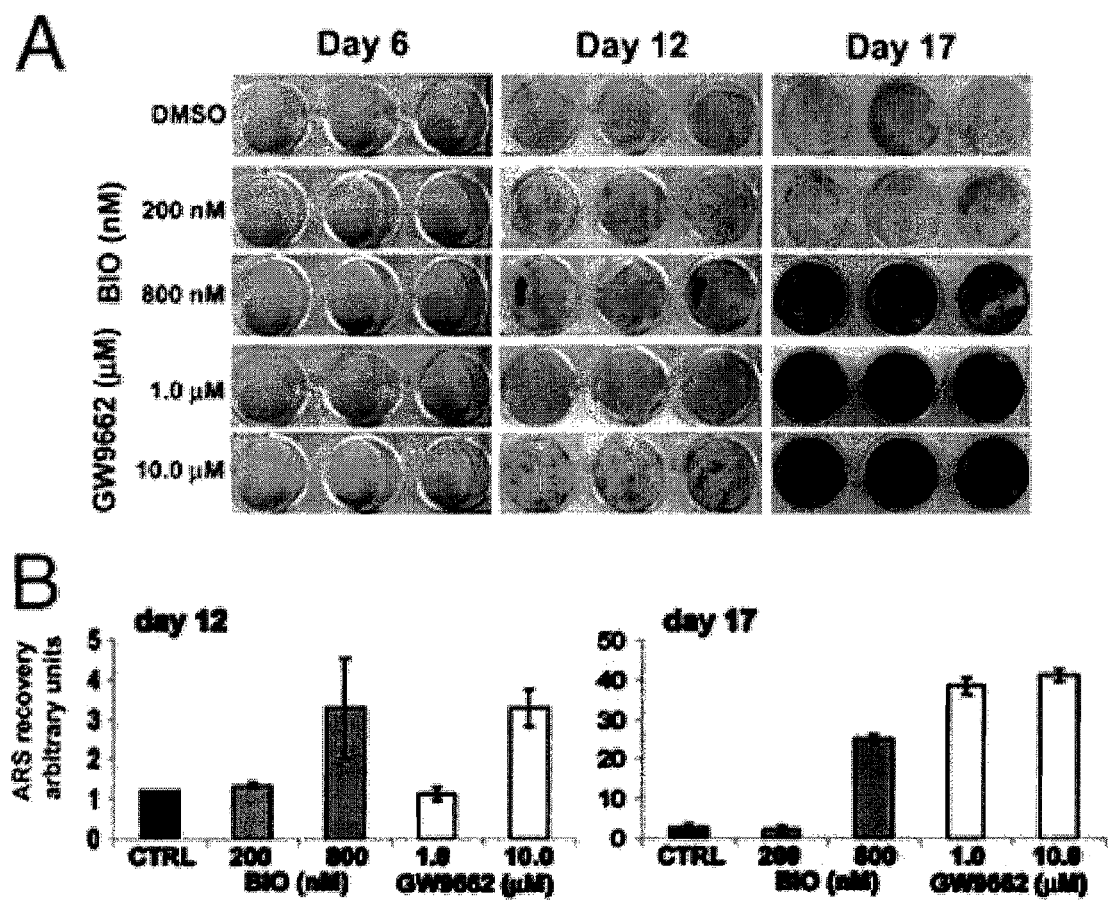
FIG. 9, comprising

The next experiments were performed to examine whether withdrawal of the Wnt stimulus caused by BIO and GW was necessary for the hMSCs to progress to a dex-dependent biomineralizing phenotype. Human MSCs were pre-cultured with BIO and GW in the presence of β-GP, ascorbate and dex for 17 days. Once again, inhibitor treatment enhanced dex-induced biomineralization (FIG. 9) suggesting that the action of BIO and GW enhances the early stages of osteogenesis and removal of the stimulus is not required to complete the process. Data from both experiments suggest that Wnt modulation is necessary to induce an early osteoprogenitor-like phenotype in hMSCs and this process can occur simultaneously with terminal differentiation.

Figure 8:
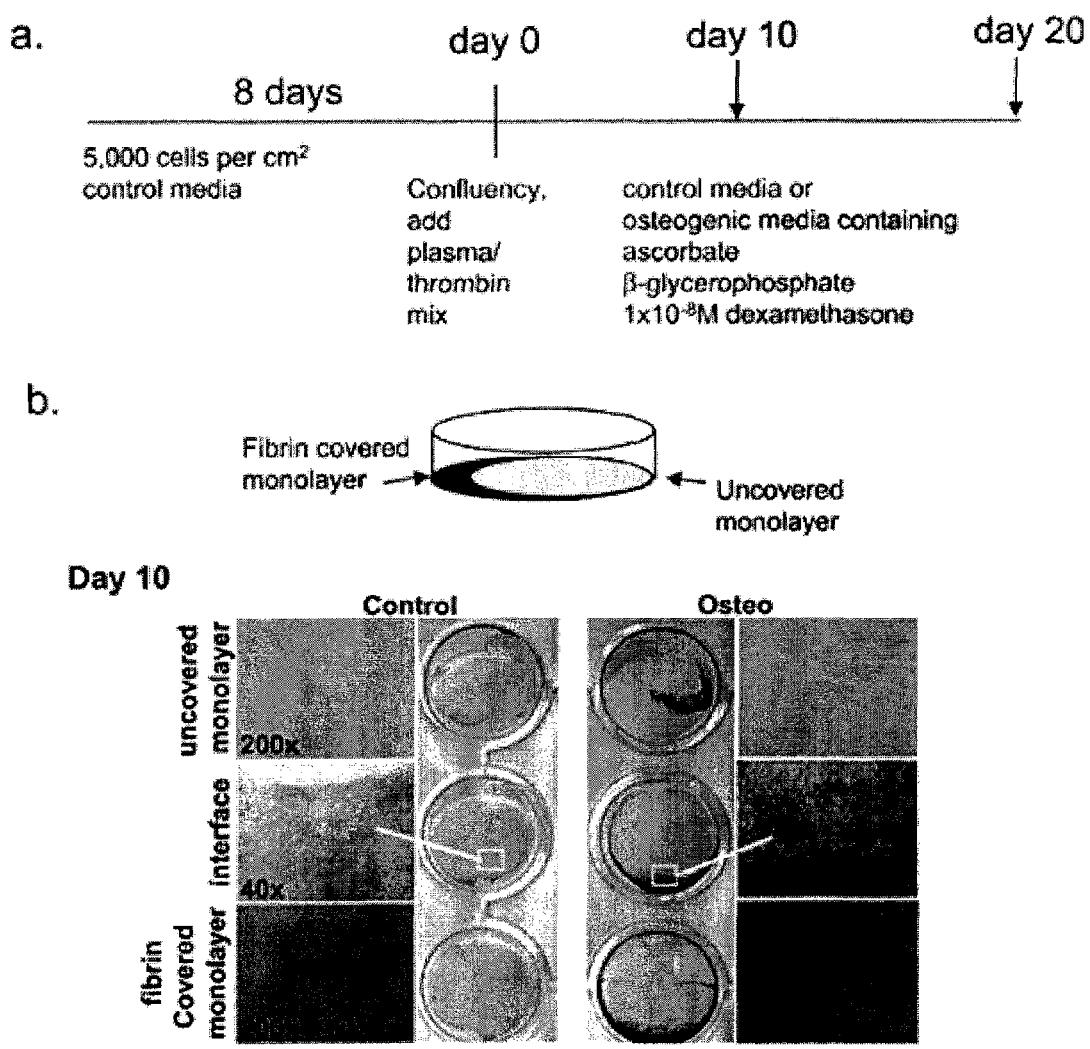
FIG. 8, comprising

Clotted Human Plasma is a Biocompatible and Osteoinductive Vector for Administration of hMSCs In anticipation of in vivo experiments testing the potential efficacy of the inhibitor treated hMSCs for the repair of bone, a number of matrices for cell administration was examined. It was observed that clotted human plasma sustained the survival and proliferation of hMSCs in, vitro and also accelerated steroid-induced biomineralization. When monolayers of hMSCs are partially covered with a meniscus of clotted human plasma, the cells in contact with the plasma mineralize faster than the uncovered portion of the monolayer when dex-containing osteogenic media is provided (FIG. 8).

Figure 10:
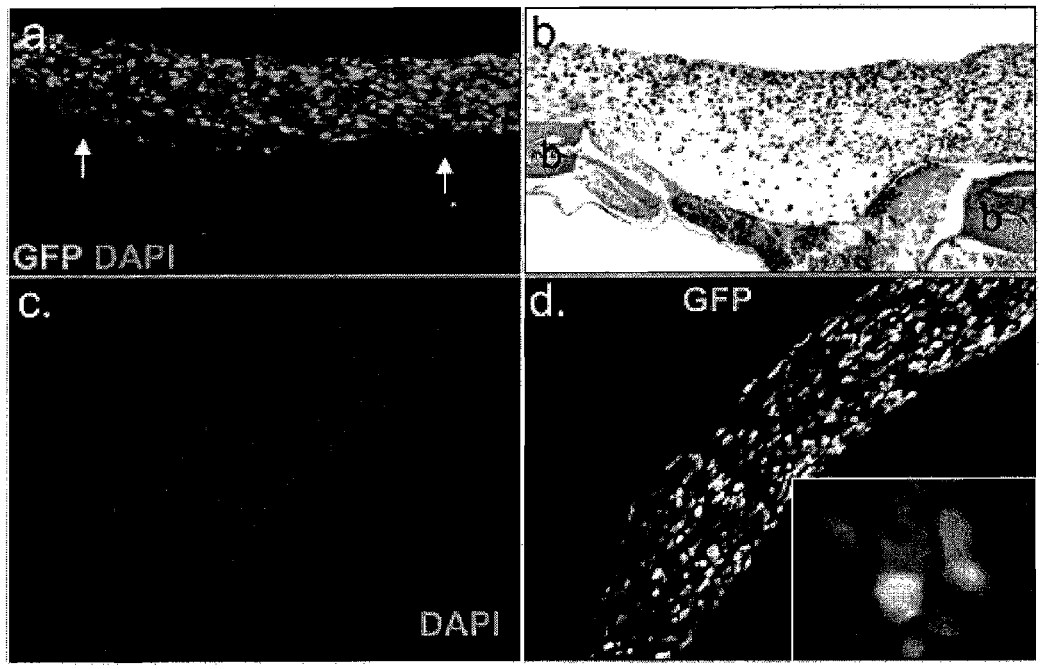
FIG. 10, comprising
Figure 11:
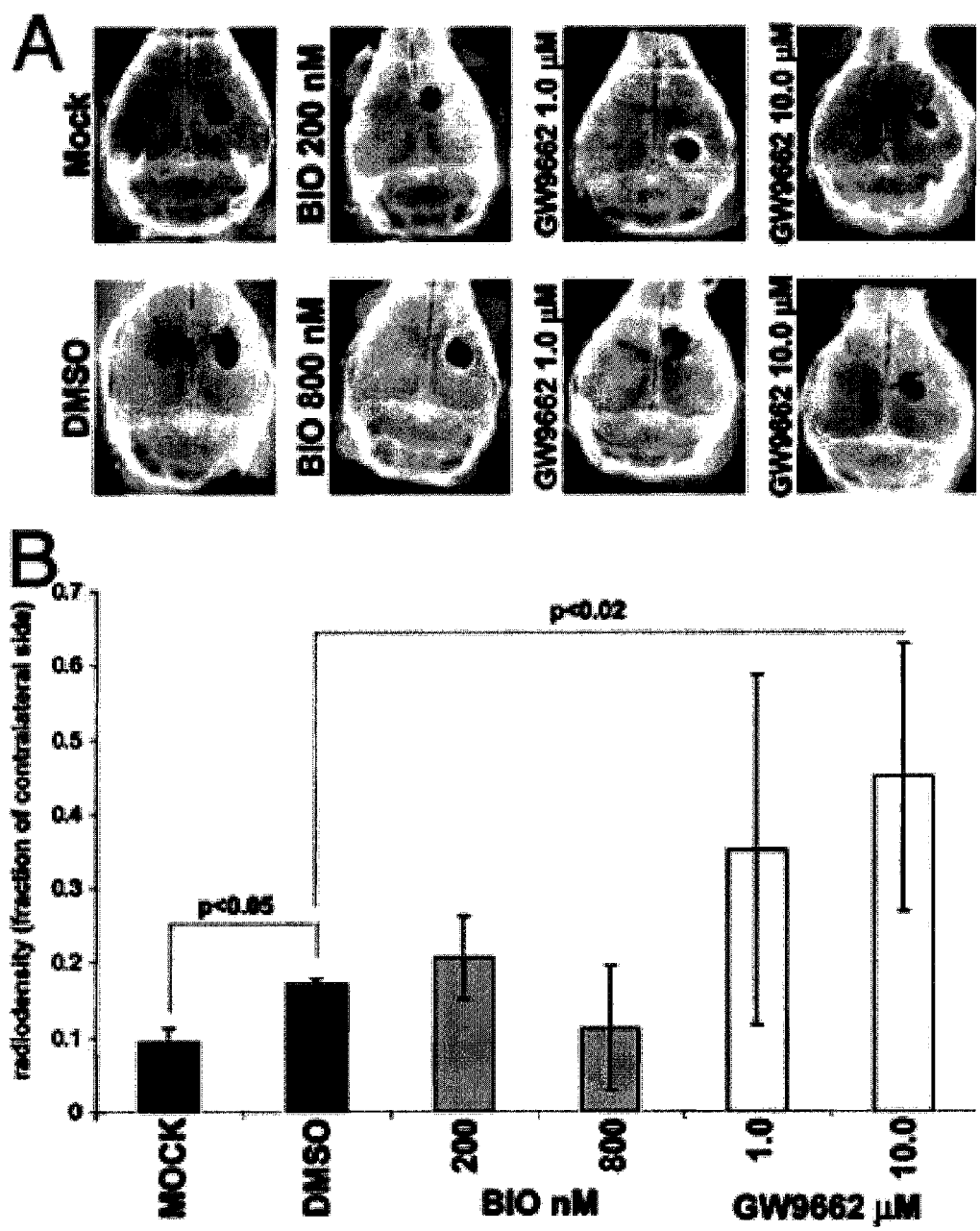
FIG. 11, comprising
Figure 13:
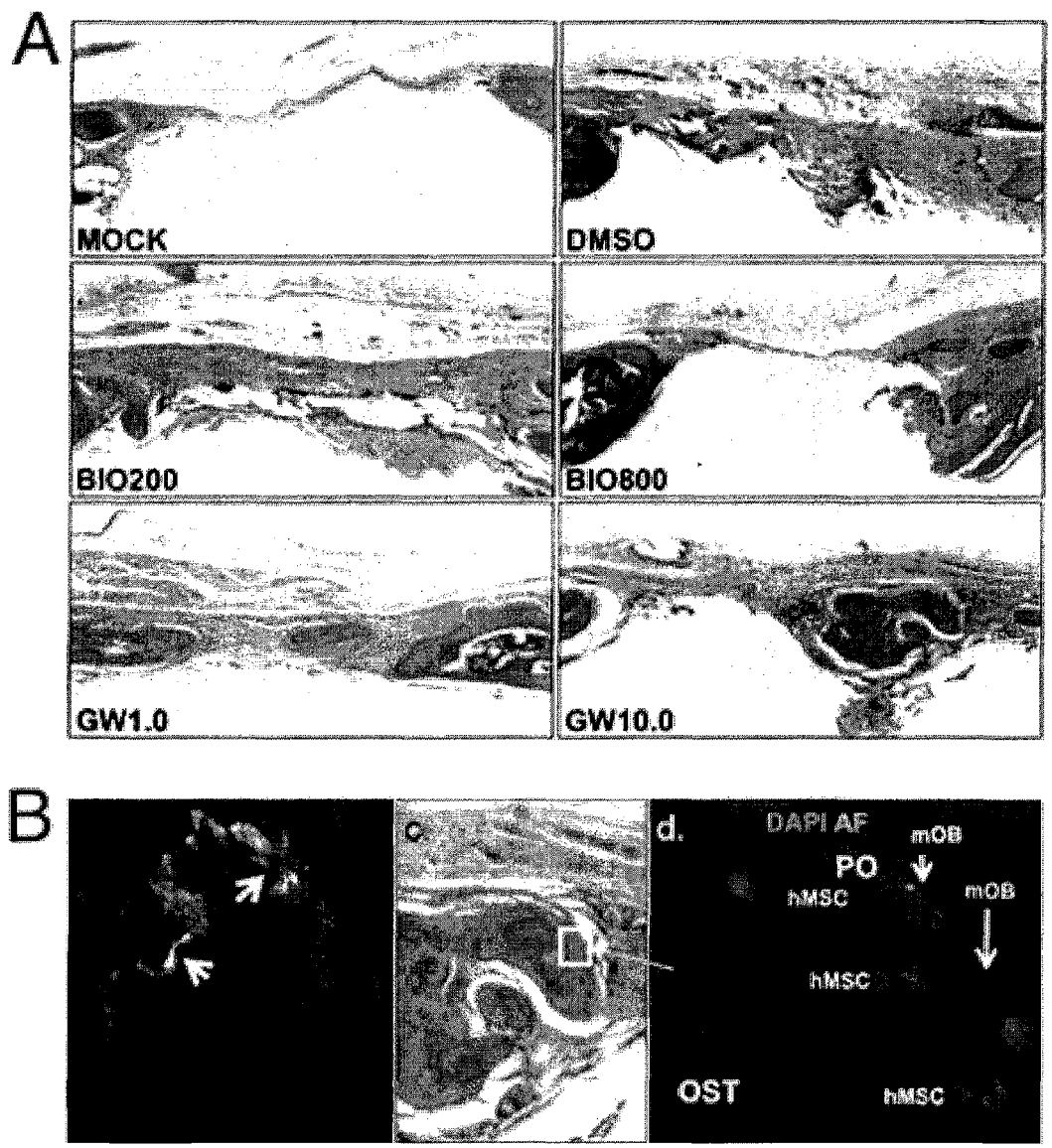
FIG. 13, comprising
Figure 14:
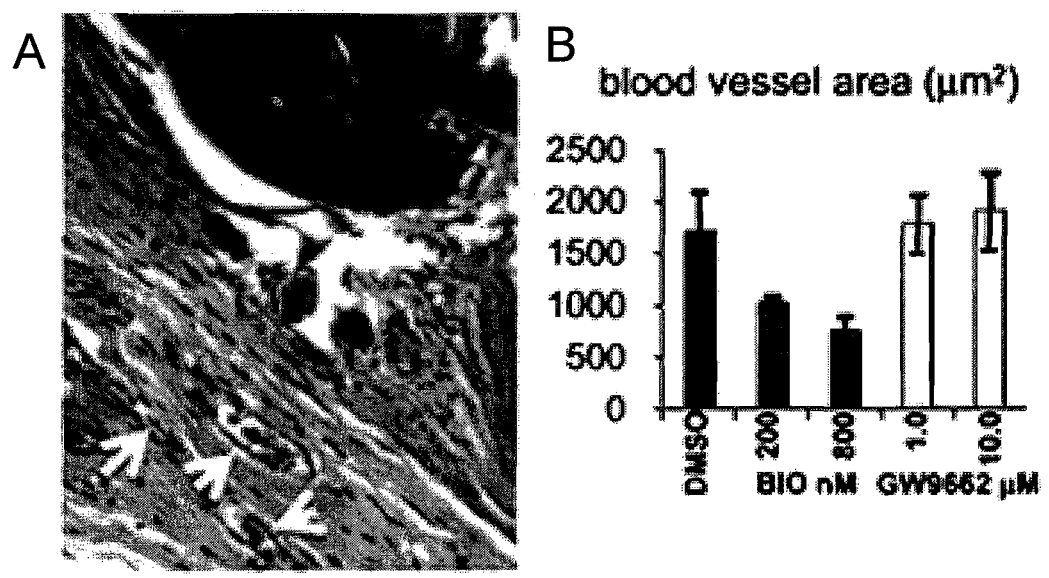
FIG. 14, comprising

The Effects of GSK3β and PPARγ Inhibition on Repair of an Experimental Induced Cranial Defect in Mice Given that BIO and GW accelerated osteogenic differentiation by human MSCs in vitro, experiments were conducted to test whether the treated hMSCs could repair a critical bone defect in vivo. Human MSCs were cultured in the presence of osteogenic medium lacking dex, but containing BIO (200 and 800 nM) or GW (1.0 and 10.0 µM). Calvarial lesions were generated in nude mice and $1 \times 10^6$ hMSCs, mixed with human plasma were applied followed by thromboplastin to initiate gelling. The scalp was sutured and the animals were allowed to heal. Initially, short-duration experiments were performed to monitor distribution of the hMSCs, and to ensure the cells had survived the implantation process. GFP-labeled hMSCs were administered and mice were sacrificed after 24 h. Upon histological analysis, a substantial number of GFP-labeled, healthy hMSCs had formed a thick layer over the injury and adjacent bone tissue (FIG. 10A, 10B). The hMSCs could be readily detected with an antibody for membrane localized human β-2 microglobulin (FIG. 10C, 10D). Robust antibody-detection of unmanipulated hMSCs, rather than lentiviral labeling was favored in long term experiments because very low passage hMSCs could be utilized, rather than genetically tagged preparations that had undergone a number of passages. Long term experiments were performed for 50 days with further doses of hMSCs administered at day 14, 28 and 42 by direct injection of a plasma:hMSC mixture under the scalp (FIG. 11A). At day 50, the crania were explanted and x-ray images of the calvarial lesions were taken. The digitized images were then analysed densitometrically to quantify the degree of bone accrual (FIG. 11B). The lesioned side was compared with the contralateral side and data were expressed as the ratio of radio-opacity on the lesioned side to the contralateral side. Surprisingly, GW, significantly improved the ability of MSCs to repair cranial lesions when compared to MSCs that were not drug treated. Upon histological analysis, new bone formation was detected in the GW groups and in the case of the 10 µM GW group, marrow sinusoids were evident in the newly formed bone (FIG. 13A) which could be identified by tetracycline incorporation (FIG. 13B). In contrast, there was no significant sign of bone repair in the mock groups that received plasma alone, and control hMSC groups, that received cells treated with DMSO or BIO. When the sections were stained with anti-β-2 microglobulin, isolated clusters of hMSCs from only control and GW groups were detected (FIGS. 13 C and 13D). However, no more than a few hundred cells could be counted throughout the entire lesion, suggesting that the majority of cells had either died or migrated away. In both control groups and in the GW treated groups, blood vessels were detected, demonstrating that GW treatment had not affected the ability of MSCs to initiate angiogenesis at trauma sites (FIG. 14A).

Enhanced compatibility of the GW-treated hMSCs for the osteogenic niche could explain the increased efficacy. However, upon further inspection of the microarray data, a minor cluster was identified where genes were profoundly down-regulated in GW-treated MSCs as compared to the control. This cluster was highly enriched for inflammatory mediators including IL1, IL8, and chemokines of the CXCL family (FIG. 25). These data could be validated by ELISA assay of supernatents from treated hMSC cultures (FIG. 26). Because nude mice are able to elicit a macrophage and neutrophil mediated response, it is probable that the GW treated MSCs were protected by reduced expression of chemoattractants.

MSCs for Regenerating Bone

Cultures of hMSCs are inherently heterogeneous, with the individuals of the population possessing different propensities for osteogenesis, chondrogenesis, adipogenesis or proliferation. Heterogeneity can arise from the nature of the donor, the number of past cell doublings, and cell density. Evidence suggests that the history of a given hMSC, with respect to the number of cell doublings, and past exposure to different levels of cell density can in most cases affect the propensity of a given cell to divide or differentiate (Sekiya et al., 2002, Stem Cells 20:530-541; Gregory et al., 2005, Sci STKE 294:pe37; Larson et al., 2008, Stem Cells 26, 193-201). This apparently stochastic distribution of cellular characteristics can be controlled in part by the addition of cytokines, growth factors and/or drugs. Given that both Wnt signaling and blunting of the adipogenic axis is necessary for the initiation of osteogenic processes in MSCs, experiments were designed to investigate the role of small molecule inhibitors in controlling the events. The results presented herein demonstrate that Wnt signaling could be increased in MSCs by either direct inhibition of GSK3β or by inhibiting the master regulator of adipogenesis, PPARγ. These observations supported the widespread notion that negative crosstalk occurs between the canonical Wnt and PPARγ axis, regulated in part by the transcription factor TAZ (Hong et al., 2005, Science 309: 1074-1078). At lower doses, expression of early osteogenic markers in hMSCs could be significantly enhanced by treatment with either inhibitor but this was attenuated at higher doses. In contrast, when hMSCs were pre-treated or simultaneously treated with BIO or GW, and subjected to dex-dependent osteogenesis, mineralization was upregulated in a dose-dependent manner. A simple interpretation of these results lead to the conclusion that endogenous canonical Wnt signaling can enhance osteogenesis. However, it is possible that the high-serum culture system used in the present experiments reflect a situation with modest osteogenic and adipogenic stimuli affecting a balanced steady state on the cells. The presence of GW and BIO therefore, disrupt the balance of the culture in favor of the osteogenic lineage. In contrast, high concentrations of PPARγ agonists in our osteogenic cultures containing dex initiate adipogenesis rather than osteogenesis.

When implanted into experimentally induced calvarial defects in mice, GW treated hMSCs profoundly improved healing and induced angiogenesis. Although vehicle treated hMSCs could not significantly enhance bone repair, angiogenesis was also induced suggesting that even vehicle treated hMSCs had survived at the site for a duration sufficient to initiate the process. Although the efficacy of GW treated hMSCs is probably due to enhanced osteogenic propensity and angiogenic properties, substantial down-regulation of immune-chemokines is also likely to extend their survival. In some instances, the survival of GW or BIO treated hMSCs was transient. Without wishing to be bound by any particular theory, it is believed that the transplanted cells provide a supporting role for host cells. In agreement with this observation, it has recently been demonstrated that a population of hMSCs with a enhanced endogenous canonical Wnt signaling serves to enhance synergistically the ostoegenic capacity of co-administered hMSCs with a lesser degree of Wnt signaling (Liu et al., 2009, J Cell Biol 185:67-75).

hMSCs treated with GW, an inhibitor of PPARγ, had increased their osteogenic propensity without blunting viability or their ability to performancillary tasks such as angiogenic stimulation. The modified cultures are essentially a combination of stromal stem cells and osteoblasts, with properties of both. Therefore, hMSCs prepared in this manner are a unique and rationally designed cytotherapeutic with profoundly enhanced efficacy for bone repair.

Example 2

Novel Biocompatible Matrices for In Vivo Delivery of MSCs for Bone Repair

In the case of critical size defects, there is a need to regrow bone to reestablish stability and support in the area of injury. Current treatment involves the use of metallic implants, but this treatment sometimes carries with it serious side effects due to the foreign nature of the implant. The following experiments were designed to determine methods for the production of a biocompatible osteoinductive matrix that maintains viability and functionality when administered to the patient.

hMSCs are multipotent cells with the ability to differentiate into many cell types, including osteoblasts. These cells are usually extracted from adult bone marrow and easily expanded and differentiated in culture using established methods. The differentiation of hMSC's into osteoblasts has been shown to rely upon Wnt signaling and this information is important for their use in repairing bone. Secreted extracellular matrix (ECM) can be extracted from hMSC cultures that have been induced to differentiate into osteoblasts. Furthermore hMSC's can be successfully co-cultured with the extracted matrix and induced to become osteoblasts. Treatment with the Wnt-modulator, 7AIPM, was found to have increased osteoinductive characteristics.

Figure 15:
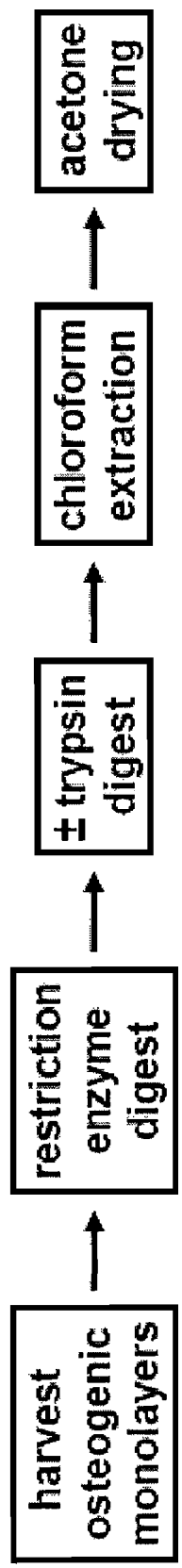
FIG. 15 is a schematic of a representative extraction process for the extraction of a biocompatible lattice from hMSCs.
Figure 16:
FIG. 16, comprising
Figure 17:
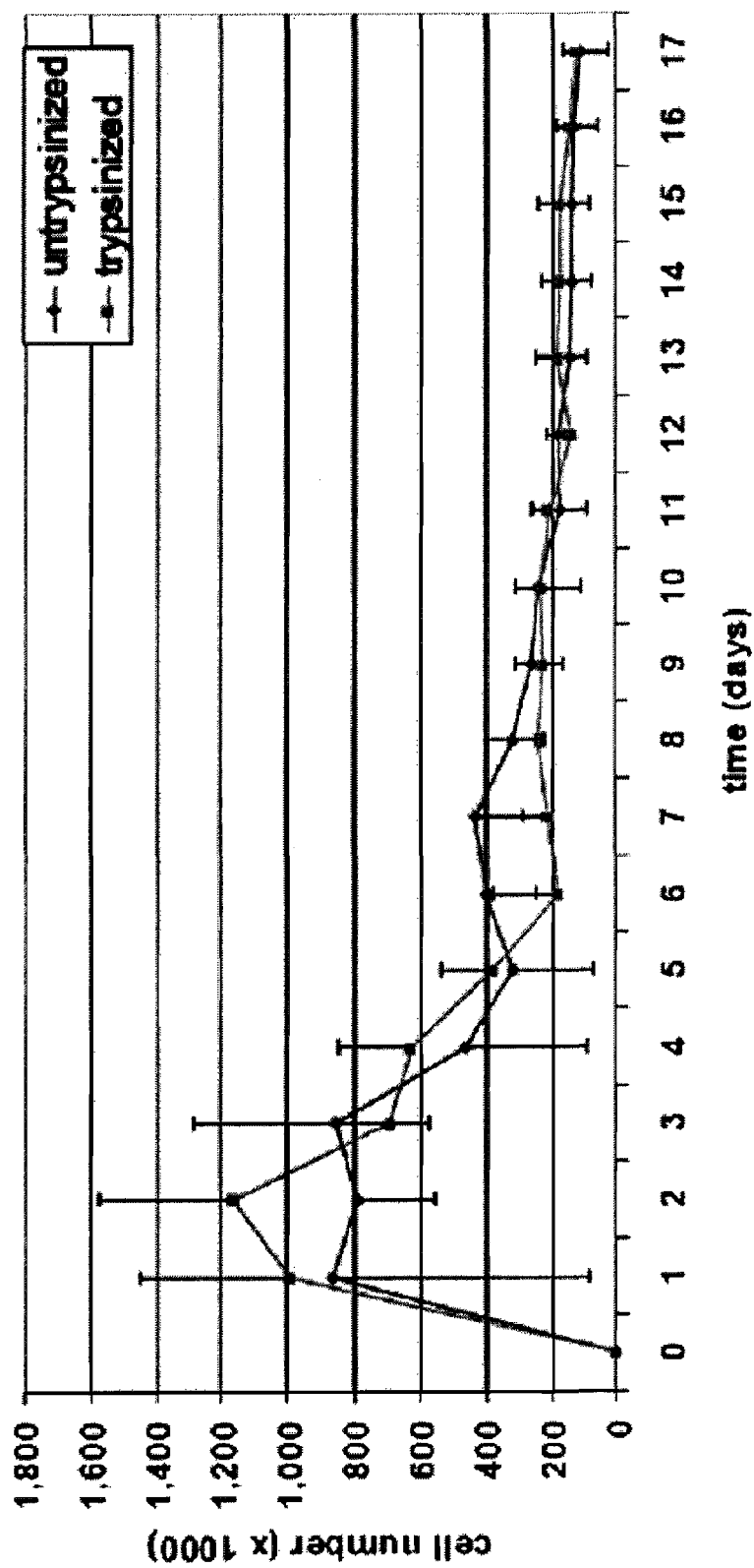
FIG. 17 is a chart demonstrating that both untreated and trypsin-treated matrices were able to sustain cell viability. One million GFP-positive MSC's were seeded onto matrices in CCM. After four days, cultures were changed to osteogenic medium. Cell numbers stabilized after osteogenic differentiation (n=5 or 4, respectively).
Figure 18:
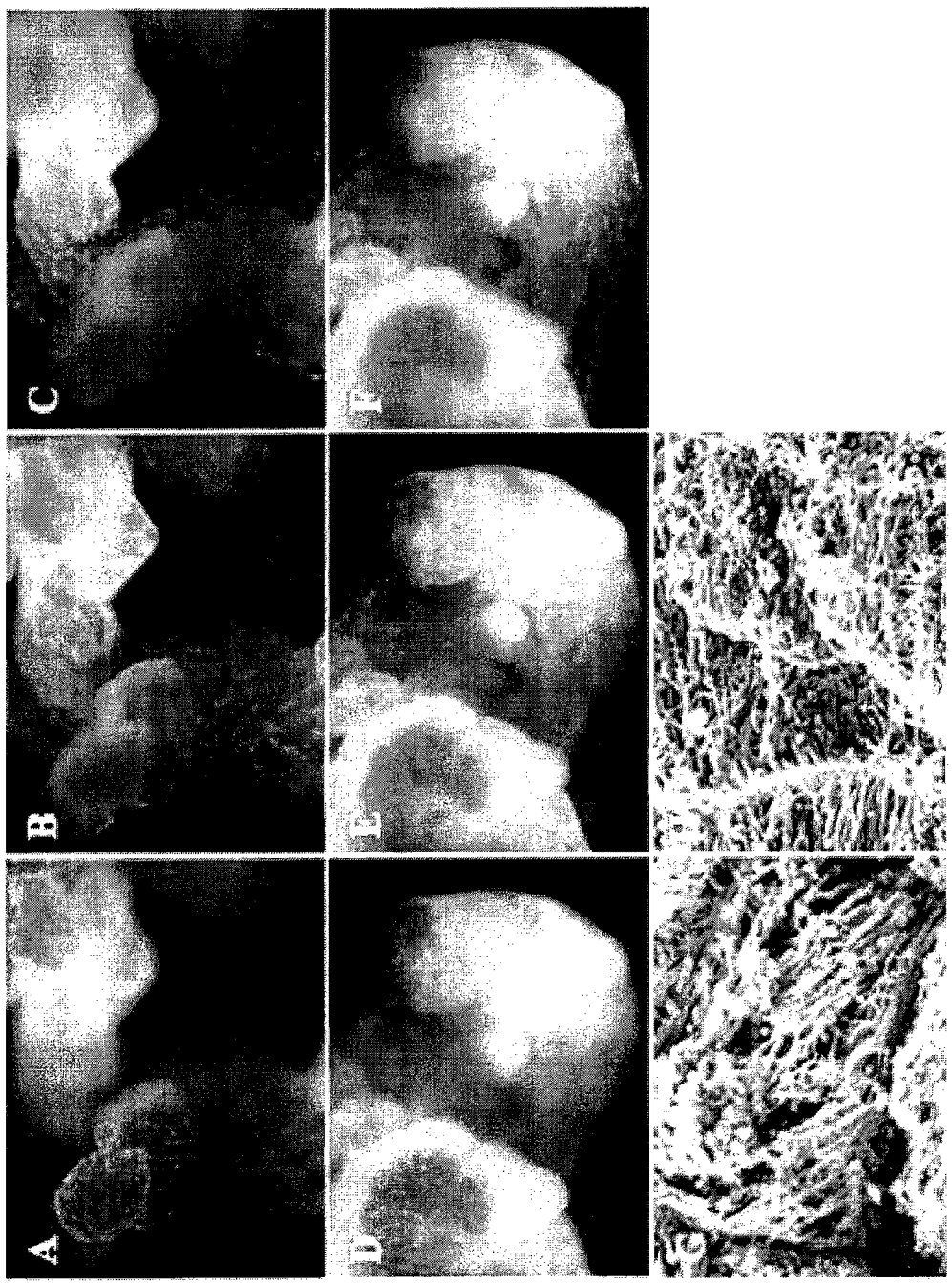
FIG. 18, comprising
Figure 19:
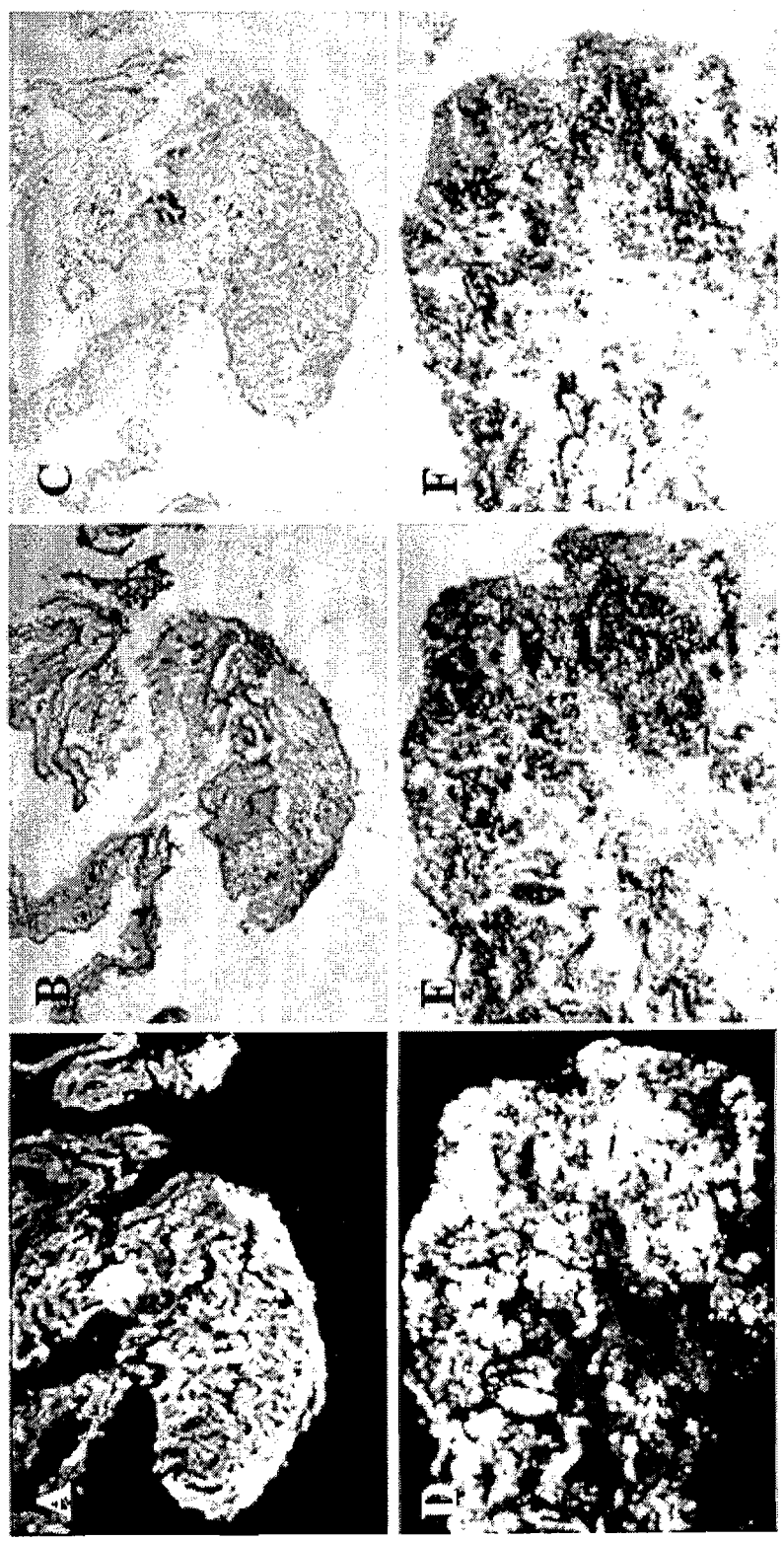
FIG. 19, comprising

The materials and methods employed in the experiments disclosed herein are now described. hMSCs from two different donors. This was done by growing hMSC's isolated from adult bone marrow as a monolayer on 15 cm dishes in complete culture medium (CCM) consisting of 80% α-minimal essential medium, 20% fetal bovine serum (FBS), 2 mM L-glutamine, 100 U/mL Penicillin, and 100 µg/mL Streptomycin. The dishes were kept at 37° C. and media changes were performed 3 times a week. After one week, the media was switch to an osteogenic media that is composed of CCM plus 5 mM β-glycerol phosphate, 50 µg/mL ascorbate-2-phosphate, and 1 nM dexamethasone. Cells were allowed to continue to grow for 3 or 6 additional weeks with media changes as described elsewhere herein. The ECM secreted by the hMSC's was then scraped off the culture dishes and extracted as set forth in FIG. 15.

The next experiments were designed to measure cell viability and differentiation ability of co-cultured hMSCs (e.g., GFP hMSCs) with the matrices collected elsewhere herein. Briefly, a total of 4 samples treated with trypsin and 5 untreated samples of matrix were placed in round bottom tubes. The GFP hMSCs were cultured as stated before for approximately 10 days. These cells were then washed with phosphate buffered saline (PBS) and lifted from their dishes using trypsin. After counting, 1 million cells were added to each sample of matrix. Cells were co-cultured with matrix samples in CCM for 3 days. On day 4 the media was changed to an osteogenic media as described elsewhere herein except for the absence of dexamethasone. After 17 total days of culture, dexamethasone was added to the media and the cells were grown for an additional 25 days for a total of 42 days. Samples of the media were obtained each day for analysis. Fluorescence intensity of the constructs was measured for each of the first 17 days to determine cell numbers and viability. Media samples from days 4-9 were analyzed for OPG using an enzyme-linked immunosorbent-assay (ELISA). Microscopic photographs of the constructs were taken on day 10. Portions of some of the constructs were frozen on day 17 and were then sectioned. Samples were screened for GFP-positive cells and analyzed for alkaline phosphatase activity.

In order to characterize the influence of 7AIPM on osteogenic differentiation, hMSC's from two donors were cultured as described elsewhere herein with the addition of varying concentrations of the compound or vehicle to the media. Samples of the media were collected daily for analysis. These samples were analyzed for the presence of OPG and Dkk-1 using ELISA. Alkaline phosphatase activity of the monolayers and cell numbers were measured using a spectrophotometer.

The results of these experiments are now described. The data suggests that hMSC's were successfully co-cultured with the extracted matrices. This is evidence by the stabilization of fluorescence intensity. Furthermore, results indicate that these cells were induced to become osteogenic. Indications of this include the increase in OPG concentration detected by ELISA as well as by the presence of ALP detected in the sections of the constructs. Based on the appearance of physical properties of the matrix it appears that 3 weeks of culture is optimal for producing useful samples. Finally, 7AIPM was found to have increased osteogenic characteristics as shown by the increased ALP activity and OPG concentration as well as the decrease of Dkk-1 concentration (FIG. 20).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A population of pre-conditioned mesenchymal stem cells, wherein the population of pre-conditioned mesenchymal stem cells is produced by:
    culturing mesenchymal stem cells in a conditioning medium lacking dexamethasone and comprising an effective amount of an inhibitor of peroxisome proliferator-activated receptor γ (PPAR-γ) for 5 to 14 days so as:
        (a) to inhibit regulation of adipogenesis in the mesenchymal stem cells,
        (b) to induce the mesenchymal stem cells to exhibit:
            (i) early or primitive osteoblastic characteristics without undergoing terminal differentiation,
            (ii) an upregulation in gene expression for collagen types I, III, V, VI, XI, and XII, and
            (iii) downregulation or depletion of cytosolic glycogen synthase kinase 3β, and
        (c) to not induce mineralization, wherein the pre-conditioned mesenchymal stem cells exhibit (a), (b), and (c) when removed from the conditioning medium.

2. The population of pre-conditioned mesenchymal stem cells of claim 1, further comprising one of either a biocompatible lattice and a biocompatible gel.

3. The population of pre-conditioned mesenchymal stem cells of claim 2, wherein the biocompatible lattice is clotted plasma.

4. The population of pre-conditioned mesenchymal stem cells of claim 1, wherein said inhibitor is 2-chloro-5-nitro-N-phenyl-benzamide (GW9662) provided in an amount of about 10 μM.

5. The population of pre-conditioned mesenchymal stem cells of claim 1, wherein said mesenchymal stem cells are retrieved from at least one of the group consisting of adult bone marrow, adipose tissue, peripheral blood, umbilical cord blood, synovial membrane, and periodontal ligament.

6. The population of pre-conditioned mesenchymal stem cells of claim 5, wherein said inhibitor of peroxisome proliferator-activated receptor γ is 2-chloro-5-nitro-N-phenyl-benzamide (GW9662).

7. The population of pre-conditioned mesenchymal stem cells of claim 1, wherein said conditioning medium further comprises beta glycerophosphate and ascorbate.

8. The population of pre-conditioned mesenchymal stem cells of claim 1, wherein said conditioning medium is provided after the mesenchymal stem cells have been allowed to divide in vitro for about six to eight doublings.

9. A composition comprising:
a biocompatible lattice; and
a population of pre-conditioned mesenchymal stem cells comingled with the biocompatible lattice, wherein the population of pre-conditioned mesenchymal stem cells is produced by:
culturing mesenchymal stem cells in a conditioning medium lacking dexamethasone and comprising an effective amount of an inhibitor of peroxisome proliferator-activated receptor γ (PPAR-γ) for 5 to 14 days so as:
(a) to inhibit regulation of adipogenesis in the mesenchymal stem cells,
(b) to induce the mesenchymal stem cells to exhibit:
(i) early or primitive osteoblastic characteristics without undergoing terminal differentiation,
(ii) an upregulation in gene expression for collagen types I, III, V, VI, XI, and XII, and
(iii) downregulation or depletion of cytosolic glycogen synthase kinase 3β, and
(c) to not induce mineralization,
wherein the pre-conditioned mesenchymal stem cells exhibit (a), (b), and (c) when removed from the conditioning medium.

10. The composition of claim 9, wherein said pre-conditioned mesenchymal stem cells are suspended in a biologically compatible diluent prior to comingling with the biocompatible lattice.

11. The composition of claim 9, wherein said composition is stored.

12. A composition comprising:
a three-dimensional scaffold; and
a population of pre-conditioned mesenchymal stem cells comingled with the three-dimensional scaffold, wherein the population of pre-conditioned mesenchymal stem cells is produced by:
culturing mesenchymal stem cells in a conditioning medium lacking dexamethasone and comprising an effective amount of an inhibitor of peroxisome proliferator-activated receptor γ (PPAR-γ) for 5 to 14 days so as:
(a) to inhibit regulation of adipogenesis in the mesenchymal stem cells,
(b) to induce the mesenchymal stem cells to exhibit:
(i) early or primitive osteoblastic characteristics without undergoing terminal differentiation,
(ii) an upregulation in gene expression for collagen types I, III, V, VI, XI, and XII, and
(iii) downregulation or depletion of cytosolic glycogen synthase kinase 3β, and
(c) to not induce mineralization,
wherein the pre-conditioned mesenchymal stem cells exhibit (a), (b), and (c) when removed from the conditioning medium.

13. The population of pre-conditioned mesenchymal stem cells of claim 1, wherein the conditioning medium is provided for about eight to ten days with periodic changes in the conditioning medium.

14. The composition of claim 12, wherein the pre-conditioned mesenchymal stem cells are initially self-renewed and expanded by dividing without the conditioning medium for six to eight doublings in vitro.

15. The population of pre-conditioned mesenchymal stem cells of claim 1, wherein the mesenchymal stem cells are initially seeded in vitro at a density of up to about 100 cells/cm$^2$ and allowed to divide for six to eight doublings without the conditioning medium.

16. The composition of claim 12, wherein the pre-conditioned mesenchymal stem cells seeded on the three-dimensional scaffold are suspended in a biologically compatible diluent prior to utilization.

17. The population of pre-conditioned mesenchymal stem cells of claim 1, wherein the conditioning medium further comprises about 5 mM beta-glycerophosphate and about 50 μg/mL ascorbate-2-phosphate.

18. The population of pre-conditioned mesenchymal stem cells of claim 1, wherein the pre-conditioned mesenchymal stem cells exhibit reduced secretion in dickkopf-1.

19. The population of pre-conditioned mesenchymal stem cells of claim 1, wherein the pre-conditioned mesenchymal stem cells further exhibit reduced secretion of one or more inflammatory mediators, including at least one of IL-1, IL-8, and chemokines of a CXCL family, the reduced secretion being compared to non pre-conditioned mesenchymal stem cells.

* * * * *